United States Patent [19]
Hellberg et al.

[11] Patent Number: 5,646,149
[45] Date of Patent: Jul. 8, 1997

[54] COMPOUNDS HAVING BOTH POTENT CALCIUM ANTAGONIST AND ANTIOXIDANT ACTIVITY AND USE THEREOF AS CYTOPROTECTIVE AGENTS

[75] Inventors: Mark R. Hellberg; George Barnes; Robert J. Collier, Jr., all of Arlington, Tex.

[73] Assignee: Alcon Laboratories, Inc., Fort Worth, Tex.

[21] Appl. No.: 472,685

[22] Filed: Jun. 7, 1995

Related U.S. Application Data

[63] Continuation of Ser. No. 163,980, Dec. 8, 1993, abandoned.

[51] Int. Cl.$^6$ ............... A61K 31/495; A61K 31/445; C07D 405/06; C07D 411/06
[52] U.S. Cl. ............... 514/253; 514/255; 514/292; 514/317; 514/320; 514/323; 514/324; 514/331; 544/361; 544/372; 544/376; 544/377; 544/396; 546/86; 546/192; 546/197; 546/200; 546/202; 546/230; 546/240
[58] Field of Search ............... 544/376, 377; 514/253

[56] References Cited

U.S. PATENT DOCUMENTS

| | | | |
|---|---|---|---|
| 3,868,377 | 2/1975 | Raabe et al. | 260/268 |
| 4,550,022 | 10/1985 | Garabedian et al. | 424/127 |
| 5,015,661 | 5/1991 | Walser | 514/443 |
| 5,120,843 | 6/1992 | McCall et al. | 544/319 |

FOREIGN PATENT DOCUMENTS

| | | |
|---|---|---|
| 0152799 | 8/1985 | European Pat. Off. . |
| 0159566 | 10/1985 | European Pat. Off. . |
| 0267155 | 5/1988 | European Pat. Off. . |
| 0369082A1 | 5/1990 | European Pat. Off. . |
| 0483772A1 | 5/1992 | European Pat. Off. . |
| 2159369 | 6/1993 | France . |
| 2900810A1 | 7/1980 | Germany . |
| 705979 | 2/1952 | United Kingdom . |
| WO8705020 | 8/1987 | WIPO . |
| WO88/08424 | 11/1988 | WIPO . |
| WO89/05803 | 6/1989 | WIPO ............... 265/16 |

OTHER PUBLICATIONS

Peruche, et al., "Mechanisms of Drug Actions Against Neuronal Damage Caused by Ischemia—An Overview", *Prog. Neuro-Psychophamacol. and Biol. Psychiat.*, vol. 17, pp. 21–70 (1993).

Miller, R., "Multiple Calcium Channels and Neuronal Function", *Science*, vol. 235, pp. 46–52 (1987).

Barrett, R., et al., "AHR–16303B, a Novel Antagonist of 5-HT$_2$ Receptors and Voltage–Sensitive Calcium Channels", *Journal of Cardiovascular Pharmacology*, vol. 17, No. 1, pp. 41–53 (1991).

Sahly, et al., "Calcium channel blockers inhibit retinal degeneration in the retinal-degeneration-B mutant of Drosophila", *Proc. Natl. Acad. Sci. USA*, vol. 89, pp. 435–439 (1992).

Beck, et al., "Local cerebal glucose utilization and local ceberal blood flow in conscious rats after administration of flunarizine", *Naunyn–Schmiedeberg's Arch Pharmacol.*, vol. 335, pp. 680–685 (1987).

Aruoma, et al., "Free Radical Scavenging And Inhibition Of Lipid Peroxidation By β–Blockers And By Agents That Interfere With Calcium Metabolism", *Biochemical Pharmacology*, vol. 42(4), pp. 735–743 (1991).

Orrenius, et al., "Calcium Ions and Oxidative Cell Injury", *Annals of Neurology*, supplement to vol. 32, pp. §33–42 (1992).

Jackson, et al., "Antioxidants: A Biological Defense Mechanism for the Prevention of Atherosclerosis", *Medicinal Research Reviews*, vol. 13, No. 2, pp. 162–182 (1993).

Li, et al., "Amelioration of Retinal Photic Injury by a Combination of Flunarizine and Dimethylthiourea", *Experimental Eye Research*, vol. 56, pp. 71–78 (1993).

Kubo, et al., "Radical Scavenging Action of Flunarizine in Rat Brain in vitro", *Arch. int. Pharmacodyn.*, vol. 272, pp. 283–295 (1984).

Mak, et al., "Comparative Antioxidant Activities of Propranolol, Nifedipine, Verapamil, and Diltiazem Against Sarcolemmal Membrane Lipid Peroxidation", *Circulation Research*, vol. 66, No. 5, pp. 1449–1452 (1990).

Breugnot, C., et al., "Calcium Antagonists Prevent Monocyte and Endothelial Cell–Induced Modification Of Low Density Lipoproteins", *Free Rad. Res. Comms.*, vol. 15, No. 2, pp. 91–100 (1991).

Zimmerman, J., et al., "In Vitro Modulation of Human Neutrophil Superoxid Anion Generation By Various Calcium Channel Antagonists Used in Ischemia–Reperfusion Resuscation", *Biochemical Pharacology*, vol. 38, No. 20, pp. 3601–3610 (1989).

Ehlert, F., et al., "The Binding of [$^3$H]Nitrendpine To Receptors for Calcium Channel Antagonists in the Heart, Cerebral Cortex, and Ileum of Rats", *Life Science*, vol. 30, pp. 2191–2202 (1982).

(List continued on next page.)

*Primary Examiner*—Emily Bernhardt
*Attorney, Agent, or Firm*—Gregg C. Brown; Michael C. Mayo

[57] ABSTRACT

Compounds having both calcium antagonist and antioxidant activity are disclosed. The compounds are useful in preventing or alleviating damage to tissues at the cellular level. Methods of treatment which employ these properties of the compounds and corresponding pharmaceutical compositions are also disclosed.

40 Claims, No Drawings

OTHER PUBLICATIONS

Lamba, O., et al., "Spectroscopic detection of lipid peroxidation products and structural changes in a sphingomyelin model system", *Biochimieu et Biophysica Act.*, 1081, pp. 181–187 (1991).

Gould, R., et al., "[$^3$H]Nitrendipine–labeled calcium channels discriminate inorganic calcium agonists and antagonists", *Proc. Natl. Acad. Sci. USA*, vol. 79, pp 3656–3660 (1982).

Scheschonka, A., et al., "Temporal Relationships Between The Loss of Vitamin E, Protein Sulfhydryls and Lipid Peroxidation in Microsomes Challenged With Different Prooxidants", *Chem.–Biol. Interactions*, vol. 74, pp. 233–252 (1990).

Shanklin Jr., J.. et al., "Synthesis, Calcium–Channel–Blocking Activity, and Antihypertensive Activity 4–(Diarylmethyl)–1–[3–(aryloxy)propyl]piperidines and Structurally Related Compounds", *Journal of Medicinal Chemistry*, vol. 34, No. 10, 3011–3022 (1991).

Eziri et al., *Chemical Abstracts*, vol. 109, No. 22844 (1988) (Abstract fo WO 87/05020, Aug. 27, 1987)..

Aono et al., *Chemical Abstracts*, vol. 117, No. 90125 (1992) (Abstract for EP 483772, May 6, 1992).

*Drug Evaluations* by American Medical Association (1993) pp. 2105–2106.

Silver et al., "Low Molecular Weight Analogs of Trolox with Potent Activity In Vitro and In Vivo," *Drug Development Research*, 27:45 (1992).

Rice–Evans et al., "Current Status of Antioxidant Therapy", *Free Radical Biology and Medicine*, 15:77 (1993).

Janero et al., "Protection of Cardiac Membrane Phospholipid Against Oxidative Injury by Calcium Antagonists", *Biochem. Pharm.*, 37(21):4197 (1989).

Scott et al., "6–hydroxychroman–2–carboxylic Acids: Novel Antioxidants", *JAOCS*, 51:200 (1974).

Van Acker et al., "Molecular Pharmacology of Vitamin E: Structural Aspects of Antioxidant Activity", *Free Radical Biology and Medicine*, 15:311(1993).

Petty et al., "Protective Effects of an β–Tocopherol Analogue Against Myocardial Reperfusion Injury in Rats", *E. J. Pharm.*, 210:85 (1992).

COMPOUNDS HAVING BOTH POTENT CALCIUM ANTAGONIST AND ANTIOXIDANT ACTIVITY AND USE THEREOF AS CYTOPROTECTIVE AGENTS the present application is a continuation of application Ser. No. 08/163,980 filed Dec. 8, 1993(now abandoned).

BACKGROUND OF INVENTION

1. Field of the Invention

The present invention is directed to the provision of compounds having potent calcium antagonist and antioxidant activity, and to the use of those compounds as cellular protective agents. The invention is further directed to the provision of methods for synthesizing the compounds of the invention and to compounds formed as intermediates during the synthesis. The invention is particularly directed to the use of the compounds of the present invention to prevent or reduce cellular damage associated with ophthalmic diseases or injuries.

2. Discussion of Related Art

In a biological system under stress induced by trauma, ischemia-reperfusion, depletion of natural defenses, inflammation, light damage (especially laser or intense operating room light), or degenerative conditions, damage occurs which can result in an increase in cellular free calcium and/or an increase in oxidative damage. Both these changes are components of the common pathway of cell death. The result of these changes is the initiation of a cascade of cellular destruction, loss of cellular function and ultimately cell loss. The loss of critical cellular components can result in organ damage and loss of organ function. Loss of function can be caused by an acute insult or may be the result of the cumulative effects of chronic insult. The following texts may be referred to for further details concerning these phenomena:

Prog. Neuro-Psychopharmacol. and Biol. Pysch., volume 17, pages 21–70 (1993);

Age, volume 16, pages 23–30 (1993);

Chem. Res. Tox., volume 32, pages 2–18 (1993); and

Ann. Neurol., volume 32, pages S33–42 (1992).

Calcium flux is a necessary part of normal cell function. The level of intracellular free calcium is highly regulated. Both receptor-operated and voltage-sensitive channels control cell signaling and stimulus response. Multiple voltage-sensitive calcium channels have been identified. These include the N, T, P, and L channels. The following publications may be referred to for further background concerning the regulation of intracellular free calcium levels:

Med. Res. Review, volume 9, pages 123–80 (1989);

Pharmacol. Review, volume 38(4), pages 321–416 (1986);

Cardiovasc. Drugs and Therapy, volume 6, pages 35–39 (1992);

Science, volume 235, pages 46–52 (1987);

Chem.-Biol. Interactions, pages 1–23 (1991); and

Biochemical Pharmacol., volume 43(1), pages 39–46 (1992).

Over-stimulation of the cell or cellular system or the defective regulation of intracellular free calcium can result in increased intracellular free calcium levels. This can lead to the initiation of a chain of biochemical processes which can lead to cell death. Agents that modulate increases in intracellular free calcium concentration can moderate the deleterious effects of over-stimulation or defective regulation. See PNAS, volume 89, pages 435–39 (1992), and references cited above. In addition, a compound that acts as a calcium antagonist can provide an additional beneficial effect by improving blood flow, reducing ischemic insult and facilitating repair. See Naunyn-Schmiedeberg's Acta Pharmacol., volume 335, pages 680–685 (1987). As utilized herein, the term "calcium antagonists" refers to organic molecules which inhibit increases in intracellular free calcium concentrations.

Agents that act as antioxidants can protect against oxidative damage associated with cellular stress. Such protection has been the subject of numerous scientific publications, including the following:

Arch. Pharmacol., volume 325, pages 129–146 (1992);

Free Rad. Biol. Med., volume 6, pages 209–224;

Free Rad. Biol. Med., volume 11, pages 215–232 (1991);

Eur. J. Pharmacol., volume 210, pages 85–90 (1992);

J. Photochem., Photobiol. Biol., volume 8, pages 211–224 (1991);

Pharmacol. and Tox., volume 70, pages 271–277 (1992); and

Medicinal Res. Rev., volume 13(2), pages 161–182 (1993).

The combined use of two or more compounds having calcium antagonist and antioxidant activity, respectively, is discussed in Experimental Eye Research, volume 5, pages 71–78 (1993). The provision of compounds having both calcium antagonist and antioxidant activity is discussed in the following patent publications: EP 267 155A and WO 89/05803 A1.

One compound known to have calcium antagonist activity, flunarizine, has also been reported to have free radical scavenging activity. See:

Arch. int. Pharmacodyn., volume 272, pages 283–295 (1984);

Eur. J. Pharmacol., volume 204, pages 315–322 (1991); and

Meth. and Find Exp. Clin. Pharmacol., volume 11(10), pages 607–612 (1989).

In addition, other classes of calcium antagonists have been reported to have antioxidant activity. See:

Free Rad. Biol. and Med., volume 12, pages 183–187 (1992);

Res. Commun. in Chem. Path. and Pharmacol., volume 76(3), pages 367–370 (1992);

J. Mol. Cell Cardiol., volume 22, pages 1199–1208 (1990);

Circulation Res., volume 66(5), pages 1449–1452 (1990);

J. Cardiovas. Pharmacol., volume 18(Suppl. 1) pages S6-S10 (1991);

Basic Res. in Cardiology, volume 87, pages 148–160 (1992);

Free Rad. Res. Comms., volume 15(2), pages 91–100 (1991); and

Biochem. Pharmacol., volume 37(21), page 4197 (1988).

However, in most cases the antioxidant effect reported is weak and not clinically relevant. This is pointed out in Biochem. Pharmacol., volume 42(4), pages 735–743 (1991), and Biochem. Phannacol., 38(20), pages 3601–3610 (1989). In addition, it is believed that a number of the effects attributed to the free radical scavenging effect of flunarizine might actually be an effect of its calcium antagonist activity since this activity was poorly understood in the early 1980's.

The present invention is directed to the provision of new compounds that have both potent calcium antagonist and potent antioxidant activity in a single molecule. The use of a single chemical entity with potent antioxidant and potent calcium antagonist activity provides increased protection relative to the use of a compound with singular activity. The advantage of a single agent with both activities over a combination of two components would be realized by the uniform delivery of an active molecule simplifying issues of drug metabolism and delivery.

SUMMARY OF THE INVENTION

The present invention provides new compounds having potent calcium antagonist and antioxidant activity. The dual therapeutic action of the compounds provides a distinct advantage over prior therapies. The dual therapeutic actions act in a complementary manner to prevent or reduce cellular damage.

The compounds of the present invention are effective cytoprotective agents. These compounds were conceived by making modifications in known calcium antagonists which confer antioxidant activity while maintaining calcium antagonist activity. More specifically, the invention is based in pan on the discovery of appropriate structural modifications of compounds having calcium antagonist activity which maintain the calcium antagonist activity of the compounds while adding potent antioxidant activity. By taking advantage of the limited allowed substitution in the piperidine or piperazine rings of known calcium antagonists, modifications have been made to instill potent antioxidant activity while retaining the calcium antagonist activity.

The compounds and associated pharmaceutical compositions of the present invention may be used to prevent or alleviate damage to various types of tissues. However, the use of the compounds to prevent or reduce damage to ophthalmic tissues at the cellular level is a particularly significant aspect of the present invention. Conditions which may be treated include cataracts, retinopathies, heredodegenerative diseases, macular degeneration, ocular ischemia, neovascular diseases, glaucoma, and damage associated with injuries to ophthalmic tissues, such as ischernia reperfusion injuries, photochemical injuries, and injuries associated with ocular surgery, particularly injuries to the retina, cornea or other tissues caused by exposure to light or surgical instruments.

The compounds of the present invention are capable of protecting against cellular damage caused by a wide range of insults. Since the compounds provide this protection by decreasing free radical or oxidalive damage and by reducing the increase in intracellular free calcium, it represents a two-prong approach to cytoprotection. Both of these mechanisms are responsible for the loss of cellular viability associated with stress regardless of the source. In addition, the expected increase in blood flow due to the calcium antagonist activity contributes to the therapeutic effect. Among other things, the advantage of a single compound over a combination of two or more compounds is that the single entity offers uniform delivery of an active molecule having both antioxidant and calcium antagonist properties. The use of a single compound rather than a combination of compounds greatly simplifies issues of pharmacokinetics, drug metabolism, and delivery.

DETAILED DESCRIPTION OF THE INVENTION

The compounds of the present invention have the following formula:

wherein:

A is an antioxidant;

Y is $(CH_2)_n$ or $CH=CH(CH_2)_n$, wherein n is 1 to 6; and

B is selected from the following groups:

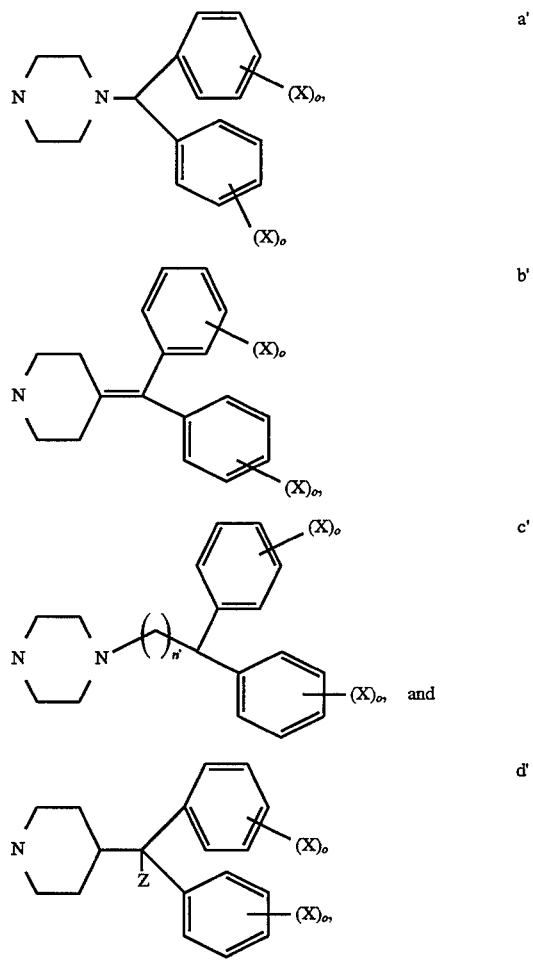

wherein:

n' is 1 to 6;

Z is H, CN or OH;

X is F, Cl, I, Br, OH, OR', SH, $S(O)_m R'$, CN or $NO_2$, wherein R' is branched or unbranched $C_1$ to $C_6$ alkyl and m is 0, 1 or 2; and o is 0 to 3.

The following groups, wherein Y and B have the same meanings as described above and R is branched or unbranched $C_1$ to $C_6$ alkyl, are representative examples of the groups which may be utilized as the antioxidant moiety of the compounds of formula (I):

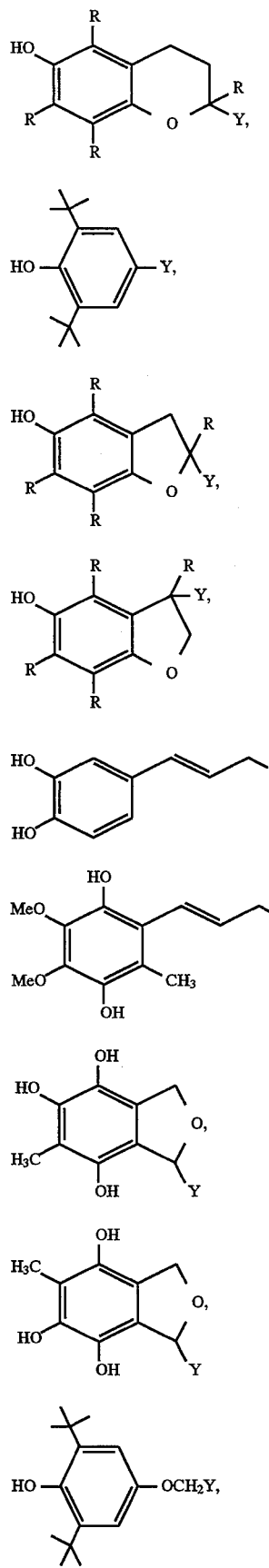
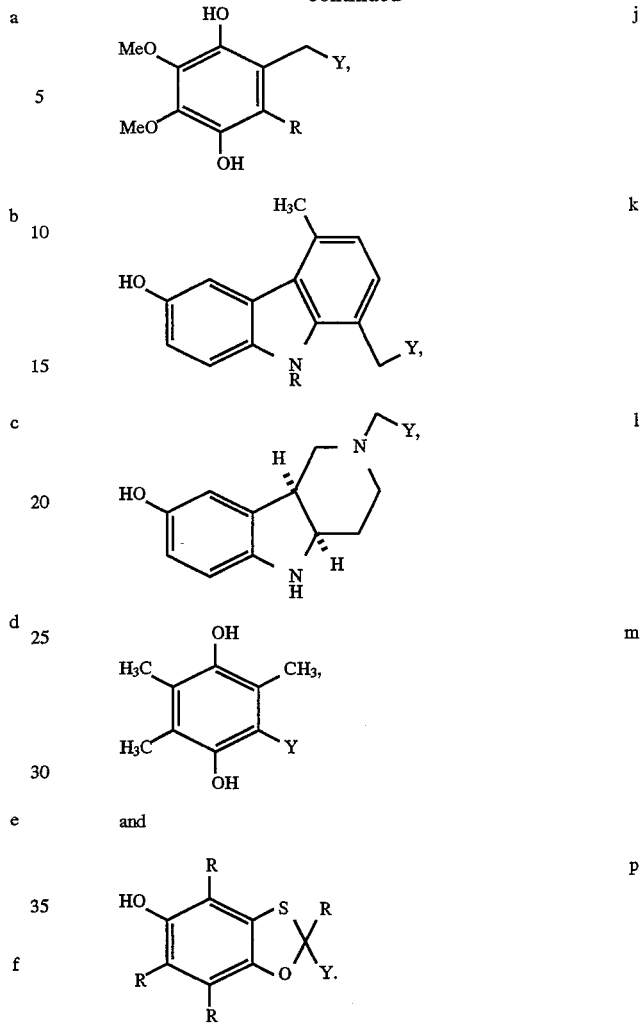
The compounds of formula (I) are further illustrated by the representative species identified in the following tables, wherein R, if present (i.e., if the antioxidant moiety A is a, e, d, j, k or p), is $C_1$ to $C_6$ branched or unbranched alkyl, but is preferably methyl.
TABLE 1
| X | X' | n | A |
|---|---|---|---|
| H | H | 1 | a |
| H | H | 2 | a |
| H | H | 3 | a |
| H | H | 5 | a |
| 4-F | 4-F | 6 | a |
| 4-F | 4-F | 1 | a |
| 4-F | 4-F | 2 | a |
| 4-F | 4-F | 3 | a |
| 4-Cl | H | 4 | a |
| 4-Cl | 4-Cl | 2 | a |
| 3, 4 di-F | 3,4 di F | 1 | a |

TABLE 1-continued

| X | X' | n | A |
|---|---|---|---|
| 3-F | 3-F | 2 | a |
| 4-Me | 4-Me | 2 | a |
| H | H | 1 | b |
| H | H | 3 | b |
| Cl | Cl | 2 | b |
| 4-F | 4-F | 2 | b |
| H | H | 1 | c |
| H | H | 2 | c |
| H | H | 3 | c |
| H | H | 5 | c |
| 4-F | 4-F | 6 | c |
| 4-F | 4-F | 1 | c |
| 4-F | 4-F | 2 | c |
| 4-F | 4-F | 3 | c |
| 4-Cl | H | 4 | c |
| H | H | 1 | d |
| H | H | 3 | d |
| Cl | Cl | 2 | d |
| 4-F | 4-F | 2 | d |
| 4-OMe | 4-OMe | 3 | d |
| H | H | 1 | e |
| H | H | 3 | e |
| Cl | Cl | 2 | e |
| 4-F | 4-F | 2 | e |
| 4-OMe | 4-OMe | 3 | e |
| H | H | 1 | f |
| H | H | 4 | f |
| Cl | Cl | 2 | f |
| 4-F | 4-F | 2 | f |
| 4-OMe | 4-OMe | 4 | f |
| H | H | 1 | g |
| H | H | 3 | g |
| Cl | Cl | 5 | g |
| 4-F | 4-F | 3 | g |
| 4-OMe | 4-OMe | 3 | g |
| H | H | 1 | h |
| H | H | 6 | h |
| Cl | Cl | 3 | h |
| 4-F | 4-F | 3 | h |
| 4-OMe | 4-OMe | 6 | h |
| H | H | 1 | i |
| H | H | 3 | i |
| Cl | Cl | 2 | i |
| 4-F | 4-F | 2 | i |
| 4-OMe | 4-OMe | 3 | i |
| H | H | 3 | j |
| H | H | 3 | j |
| 4-F | 4-F | 6 | j |
| 4-F | 4-F | 1 | j |
| 4-F | 4-F | 2 | j |
| 4-F | 4-F | 3 | j |
| 4-Cl | H | 3 | j |
| 4-Cl | 4-Cl | 3 | j |
| H | H | 3 | k |
| 4-F | 4-F | 3 | k |
| 4-F | 4-F | 2 | l |
| 3-F | 3-F | 3 | l |
| H | H | 3 | l |
| H | H | 3 | m |
| H | H | 4 | m |
| 3-F | 3-F | 4 | m |
| H | H | 2 | n |
| H | H | 3 | n |
| H | H | 4 | n |
| H | H | 6 | n |
| 4-F | 4-F | 5 | n |

TABLE 1-continued

| X | X' | n | A |
|---|---|---|---|
| 4-F | 4-F | 2 | n |
| 3-Br | 3-Br | 3 | n |

TABLE 2

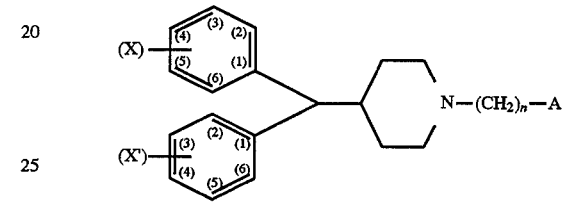

| X | X' | n | A |
|---|---|---|---|
| H | H | 1 | a |
| H | H | 2 | a |
| H | H | 3 | a |
| H | H | 5 | a |
| 4-F | 4-F | 6 | a |
| 4-F | 4-F | 1 | a |
| 4-F | 4-F | 2 | a |
| 4-F | 4-F | 3 | a |
| 4-Cl | H | 4 | a |
| 4-Cl | 4-Cl | 2 | a |
| 3, 4 di-F | 3,4 di F | 1 | a |
| 3-F | 3-F | 2 | a |
| 4-Me | 4-Me | 2 | a |
| H | H | 1 | b |
| H | H | 3 | b |
| Cl | Cl | 2 | b |
| 4-F | 4-F | 2 | b |
| H | H | 1 | c |
| H | H | 2 | c |
| H | H | 3 | c |
| H | H | 5 | c |
| 4-F | 4-F | 6 | c |
| 4-F | 4-F | 1 | c |
| 4-F | 4-F | 2 | c |
| 4-F | 4-F | 3 | c |
| 4-Cl | H | 4 | c |
| H | H | 1 | d |
| H | H | 3 | d |
| Cl | Cl | 2 | d |
| 4-F | 4-F | 2 | d |
| 4-OMe | 4-OMe | 3 | d |
| H | H | 1 | e |
| H | H | 3 | e |
| Cl | Cl | 2 | e |
| 4-F | 4-F | 2 | e |
| 4-OMe | 4-OMe | 3 | e |
| H | H | 1 | f |
| H | H | 4 | f |
| Cl | Cl | 2 | f |
| 4-F | 4-F | 2 | f |
| 4-OMe | 4-OMe | 4 | f |
| H | H | 1 | g |
| H | H | 3 | g |
| Cl | Cl | 5 | g |
| 4-F | 4-F | 3 | g |
| 4-OMe | 4-OMe | 3 | g |
| H | H | 1 | h |

TABLE 2-continued

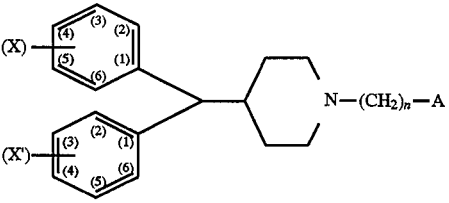

| X | X' | n | A |
|---|----|---|---|
| H | H | 6 | h |
| Cl | Cl | 3 | h |
| 4-F | 4-F | 3 | h |
| 4-OMe | 4-OMe | 6 | h |
| H | H | 1 | i |
| H | H | 3 | i |
| Cl | Cl | 2 | i |
| 4-F | 4-F | 2 | i |
| 4-OMe | 4-OMe | 3 | i |
| H | H | 3 | j |
| H | H | 3 | j |
| 4-F | 4-F | 6 | j |
| 4-F | 4-F | 1 | j |
| 4-F | 4-F | 2 | j |
| 4-F | 4-F | 3 | j |
| 4-Cl | H | 3 | j |
| 4-Cl | 4-Cl | 3 | j |
| H | H | 3 | k |
| 4-F | 4-F | 3 | k |
| 4-F | 4-F | 2 | l |
| 3-F | 3-F | 3 | l |
| H | H | 3 | l |
| H | H | 3 | m |
| H | H | 4 | m |
| 3-F | 3-F | 4 | m |
| H | H | 2 | n |
| H | H | 3 | n |
| H | H | 4 | n |
| H | H | 6 | n |
| 4-F | 4-F | 5 | n |
| 4-F | 4-F | 2 | n |
| 3-Br | 3-Br | 3 | n |

TABLE 3

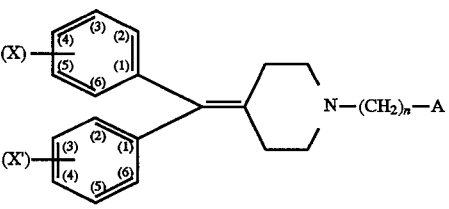

| X | X' | n | A |
|---|----|---|---|
| H | H | 1 | a |
| 4-F | 4-F | 2 | a |
| 3,4-F | 3,4-F | 3 | a |
| 3-Cl | 3-Cl | 4 | a |
| H | H | 2 | b |
| 4-F | 4-F | 1 | b |
| 4-OMe | 4-OMe | 3 | b |
| H | H | 2 | c |
| H | H | 4 | c |
| 4-F | 4-F | 3 | c |
| 4-NO₂ | 4-NO₂ | 1 | d |
| 4-CN | 4-CN | 2 | d |
| 3-Br | 3-Br | 2 | d |
| H | H | 4 | f |
| 3-F | H | 2 | f |
| 4-F | 4-F | 2 | i |
| H | H | 3 | l |

TABLE 3-continued

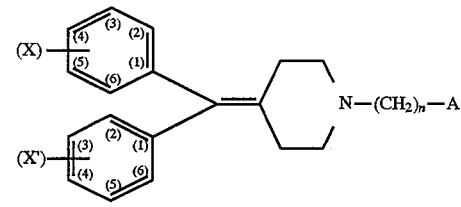

| X | X' | n | A |
|---|----|---|---|
| H | H | 1 | n |
| 4-F | 4-F | 2 | n |
| 3,4-F | 3,4-F | 3 | n |
| 3-Cl | 3-Cl | 4 | n |

TABLE 4

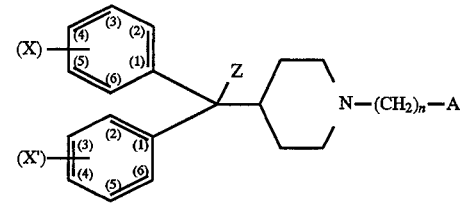

| X | X' | n | A | Z |
|---|----|---|---|---|
| H | H | 1 | a | OH |
| 4-F | 4-F | 2 | a | CN |
| 3,4-F | 3,4-F | 3 | a | OH |
| 3-Cl | 3-Cl | 4 | a | OH |
| H | H | 2 | b | CN |
| 4-F | 4-F | 1 | b | CN |
| 4-OMe | 4-OMe | 3 | b | OH |
| 4-F | 4-F | 3 | c | CN |
| 4-NO₂ | 4-NO₂ | 1 | d | OH |
| 4-CN | 4-CN | 2 | d | CN |
| 3-Br | 3-Br | 2 | d | OH |
| H | H | 4 | f | CN |
| 3-F | H | 2 | f | CN |
| H | H | 2 | c | CN |
| H | H | 4 | c | CN |
| 4-F | 4-F | 2 | i | OH |
| H | H | 3 | l | OH |
| H | H | 1 | n | CN |
| 4-F | 4-F | 2 | n | CN |
| 3,4-F | 3,4-F | 3 | n | OH |
| 3-Cl | 3-Cl | 4 | n | OH |

TABLE 5

| X | X' | n | n' | A |
|---|----|---|----|---|
| H | H | 1 | 1 | a |
| 4-F | 4-F | 2 | 1 | a |
| 3,4-F | 3,4-F | 3 | 1 | a |
| 3-Cl | 3-Cl | 4 | 1 | a |
| H | H | 1 | 2 | a |
| 4-F | 4-F | 2 | 2 | a |

TABLE 5-continued

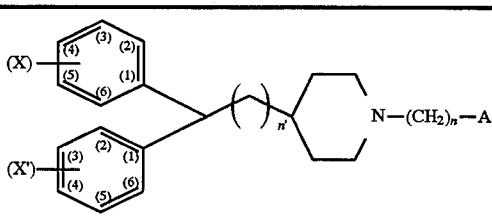

| X | X' | n | n' | A |
|---|----|---|----|---|
| 3,4-F | 3,4-F | 3 | 2 | a |
| 3-Cl | 3-Cl | 4 | 2 | a |
| H | H | 1 | 2 | a |
| H | H | 1 | 3 | a |
| H | H | 1 | 4 | a |
| H | H | 2 | 5 | a |
| H | H | 1 | 6 | a |
| 4-F | 4-F | 1 | 3 | a |
| 4-F | 4-F | 2 | 2 | a |
| 4-F | 4-F | 1 | 3 | b |
| 4-OMe | 4-OMe | 3 | 2 | b |
| H | H | 2 | 2 | c |
| H | H | 4 | 1 | c |
| 4-F | 4-F | 3 | 2 | c |
| 4-NO$_2$ | 4-NO$_2$ | 1 | 4 | d |
| 4-CN | 4-CN | 2 | 5 | d |
| 3-Br | 3-Br | 2 | 5 | d |
| H | H | 4 | 5 | f |
| 3-F | H | 2 | 3 | f |
| 4-F | 4-F | 2 | 3 | i |
| H | H | 3 | 4 | l |
| H | H | 1 | 2 | n |
| 4-F | 4-F | 2 | 1 | n |
| 3,4-F | 3,4-F | 3 | 1 | n |
| 3-Cl | 3-Cl | 4 | 1 | n |

Criteria for selecting specific antioxidant moieties and for evaluating antioxidant and calcium antagonist activity in relation to compounds of formula (I) are described below.

The antioxidant moieties of the above-described compounds are substances such as an organic molecule, which are known to be capable of reacting with the free radicals encountered in physiological systems. For a substance to have a protective effect as an antioxidant in a physiological system, it must act to prevent the damaging activity of free radicals by: (i) inhibiting the process leading to their generation, (ii) suppressing the amplification of the process by scavenging primary free radicals, or (iii) inhibiting the amplification of free radical-initiated damage by intercepting secondary free radicals. The therapeutic activity of an antioxidant in a biological system depends on the source and nature of the damaging free radical, the site of damage, and the delivery of a therapeutically effective concentration of the antioxidant to the appropriate site. This invention is concerned with substances that demonstrate antioxidant activity by reacting with free radicals to reduce the damage caused by these species. The antioxidant component contributes to the cytoprotective activity of these compounds by quenching the primary free radicals or the free radicals generated as the primary damage process is amplified.

The preferred antioxidant moieties in the compounds of formula (I) are phenolic compounds. The antioxidant activity of these compounds is thought to reside in their ability to react with free radicals and therefore terminate radical chain reactions. The reaction of these phenolic compounds with peroxyl free radicals in biological systems is particularly important. The phenoxyl radicals formed by the reaction of a free radical with a phenol are resonance stabilized and typically do not continue the chain reaction. In biological systems, the parent phenol from phenolic antioxidants such as α-tocopherol (vitamin E) can be regenerated from the phenoxyl free radical by vitamin C and/or glutathione (GSH), thereby providing a way to complete the detoxification process. See Free Radical Biology & Medicine, volume 15, pages 311–328 (1993).

The antioxidant activity of the phenolic compounds is enhanced by stabilizing the phenoxyl free radical or by facilitating the transfer of the free radical to other components of the detoxification mechanism, such as GSH or vitamin C. Alkyl substituents stabilize the phenoxyl free radical by electron donation and the steric bulk of ortho substituents reduces the propensity of the phenoxyl radical to participate in free radical chain reactions. An increase in steric bulk from ortho dimethyl to ortho di-tert-butyl groups decreases the reactivity due to the excessive crowding of the reactive phenolic hydroxyl groups. In addition, overcrowding reduces the rate of exchange with the biological detoxification mechanisms, thereby reducing the efficiency of the antioxidant. The introduction of a para-substituent such as an OH or O-alkyl group increases the stability of the phenoxyl free radical by delocalizing the electron density through p orbital overlap. By including the para oxygen in a five or six membered ring, the p orbital of the oxygen is constrained in a position that approaches being perpendicular to the aromatic ring, providing near optimum overlap and allowing efficient delocalization of the electron density. Combining ortho methyl substituents with a para alkoxy group constrained in a five or six membered ring provides a phenolic compound with potent antioxidant activity. Antioxidant activity can be enhanced by selectively incorporating modifications such as those discussed above.

Based on the foregoing considerations and the known structure-activity relationships of the calcium antagonists, the above described phenolic groups are preferred as the antioxidant moiety of the present compounds. The most preferred antioxidant moieties are benzofuran and benzopyran derivatives, which provide potent antioxidant activity but do not interfere with calcium antagonist activity.

The compounds of the present invention have free radical scavenging activity that can be measured by the ability of the above-described antioxidant moieties of the compounds to quench a stable free radical dye, such as 1,1'-diphenyl-2-picrylhydrazine (DPPH), as described in Free Radical Research Communications, volume 15, pages 91–100 (1991), or by the ability of the compound to protect against oxidative insult in liposomes or microsomes, as described in Biochimica, Biophysica Acta, volume 1081, pages 181–187 (1991) and Chemical and Biological Interactions, volume 74, pages 233–252 (1990), respectively. Thus, the antioxidant moieties in the compounds of the present invention will:

1) provide greater than 20% quench of the free radical at concentrations of DPPH and the test agent equal to $10^{-4}M$, in accordance with the above-cited DPPH assay;
2) demonstrate an IC$_{50}$ of less than 20 μM, in accordance with the above cited liposome assay; or
3) demonstrate an IC$_{50}$ of less than 20 μM, in accordance with the above-cited liver microsome assay.

Antioxidant moieties which satisfy the foregoing criteria are referred to herein as having "therapeutically significant flee radical scavenging activity".

The calcium antagonist moieties of the compounds of the present invention are organic compounds which inhibit increases in intracellular-free calcium. Increased intracellular-free calcium may arise from the influx of calcium from extracellular sources or the release of sequestered calcium from intracellular stores. Intracellular-free calcium concentration is regulated by many mechanisms, including, for example, receptor-operated calcium channels, voltage-sensitive calcium channels, sodium-calcium exchangers, and calcium flux through sodium channels. A sustained increase in intracellular-free calcium results in events such as the deregulation of cellular metabolism and the activation of cambolic enzymes, such as calcium-activated proteases and phospholipases. This process can ultimately lead to cell loss. Calcium antagonism can inhibit the increase in intracellular calcium by various mechanisms including but not limited to:

- a) preventing the flux through voltage-sensitive calcium channels (N,L,T,P);
- b) blocking flux through receptor operated calcium channels;
- c) preventing the release of calcium sequestered in sarcoplasmic reticulum; or
- d) blocking nonspecific channels (i.e., reversing sodium/calcium exchangers or blocking calcium flux through a sodium channel).

The compounds of the present invention act as calcium antagonists by inhibiting increases in intracellular calcium. The calcium antagonist activity of the compounds may be determined in accordance with one or more of the assays listed below:

1) radioligand binding assays, wherein radiolabeled nitrendipine is displaced from rat brain cortices (minimum activity: $IC_{50}$ of less than 20 µM), as described in *Life Science*, volume 30, pages 2191–2202 (1979) and *Procedures of the National Academy of Science, USA*, volume 79, pages 3656–3650 (1982);

2) calcium antagonist binding assays, such as the relaxation of pre-contracted rabbit aortic strips of greater than 7.0, as described in *Journal of Medicinal Chemistry*, volume 34, pages 3011–3022 (1991) and references cited therein (minimum activity: $IC_{50}$ value less than 20 µM);

3) inhibition of calcium flux in a cellular system, as measured by a fluorescent dye, in accordance with the procedures described in *Journal of Cardiovascular Pharmacology*, volume 17, pages 41–53 (1991), and references cited therein, (minimum activity: $IC_{50}$ of less than 100 nm); or 4) inhibition of calcium induced contractions of rabbit thoracic aortic strips, in accordance with the procedures described in *Journal Cardiovascular Pharmacology*, volume 17, pages 41–53 (1991), and references cited therein (minimum activity: $pA_2$ greater than 7).

Although the above-described activities define the upper limits for compounds expected to have cytoprotective activity afforded by the combined antioxidant/calcium antagonist mechanisms described herein, it is also necessary for the compounds to be delivered to the target tissue and for tissue levels to reach therapeutically effective levels, in order for the compounds to demonstrate cytoprotective activity. It is also to be understood that each of the compounds of formula (I) is useful to different degrees for treating patients afflicted with or prone to various types of cellular damage. The success of treatment will depend on the type of cellular insult and the route of administration used to treat those conditions.

The preferred compounds are those wherein: the antioxidant moiety A is a, b, c, d or p, and R, if present, is methyl; n is 1 to 4; and the calcium antagonist moiety is a' or d', Z is H or OH, and X is F, Cl, CN, $S(O)_mR'$, or OR', wherein m is 1 or 2 and R' is branched or unbranched $C_1$ to $C_4$ alkyl.

The following compounds are particularly preferred:

Compound No. 1

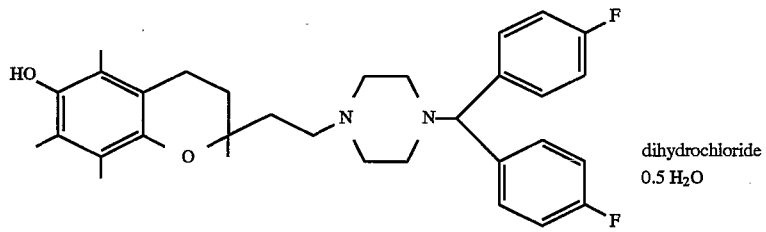

dihydrochloride
0.5 H$_2$O 1-(4,4'-difluorobenzhydryl)-4-(6-hydroxy-2,5,7,8-tetramethylchroman-2-ethyl) piperazine dihydrochloride hemihydrate Compound No. 2

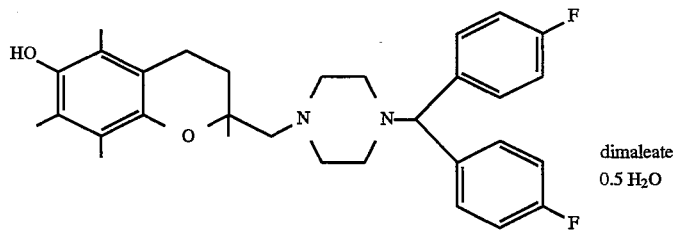

dimaleate
0.5 H$_2$O 1-(4,4'-difluorobenzhydryl)-4-(6-hydroxy-2,5,7,8-tetramethylchroman-2-methyl) piperazine dimaleate hemihydrate -continued Compound No. 3

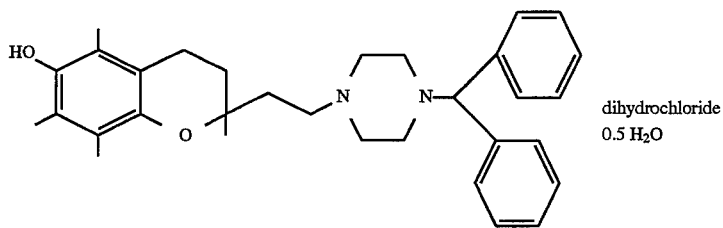

dihydrochloride
0.5 H₂O 1-benzhydryl-4-(6-hydroxy-2,5,7,8-tetramethylchroman-2-ethyl)
piperazine hydrochloride hemihydrate Compound No. 4

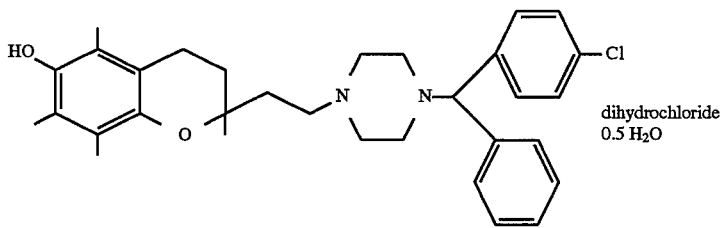

dihydrochloride
0.5 H₂O 1-(4-chlorobenzhydryl)-4-(6-hydroxy-2,5,7,8-tetramethylchroman-2-ethyl)
piperazine hydrochloride hemihydrate Compound No. 5

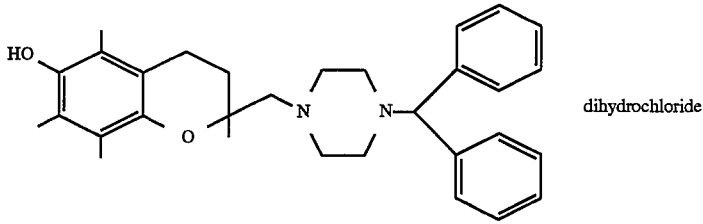

dihydrochloride 1-benzhydryl-4-(6-hydroxy-2,5,7,8-tetramethylchroman-2-methyl)
piperazine dihydrochloride Compound No. 6

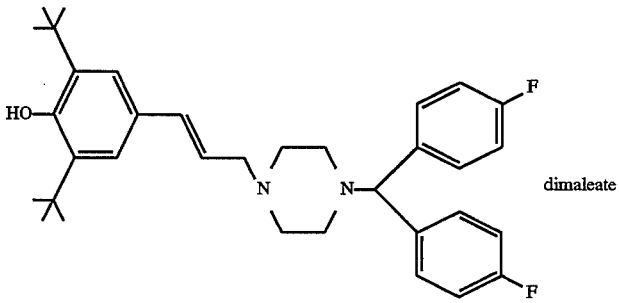

dimaleate

E-3-(4-(4', 4"-difluorobenzhydryl)piperazine)-1-[4-hydroxy-3,5-bis
(1,1-dimethylethyl)phenyl]propene dimaleate Compound No. 7

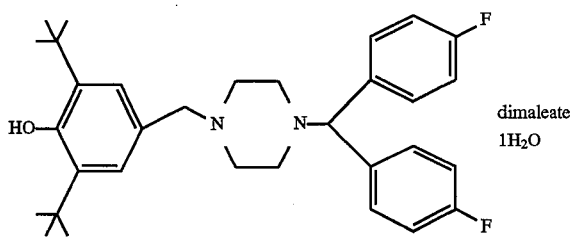

1-(4,4'-difluorobenzhydryl-4-(3,5-bis(1,1-dimethylethyl)-4-hydroxyphenyl) piperazine dimaleate monohydrate Compounds of the formula A—Y—B, as defined above, may be prepared in accordance with the following general schemes as well as modifications thereof which will be apparent to those skilled in the art:

Method 1

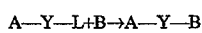

Amines of the general form B, as defined above, can be reacted with the activated alcohol derivative A—Y—L, where L is a leaving group such as a Cl, Br, I or organic sulfonate (such as mesylate or rosylate) and A—Y are as described above, under standard conditions using solvents such as acetonitrile, dimethylformamide, 1-butanol or tetrahydrofuran in the presence of a base such as potassium carbonate, potassium bicarbonate, sodium carbonate or sodium bicarbonate. The use of certain protecting groups and deprotection steps may be necessary, as will be appreciated by those skilled in the art. Compounds A—Y—L and B are commercially available or can be prepared using known reactants and procedures.

Method 2

Amines of the general formula B, as defined above, can be condensed with the aldehyde A—W—CHO, wherein W is $(CH_2)_{n-1}$ or $CH=CH(CH_2)_{n-1}$, n is 1 to 6, and A is as described above, and then the resulting species can be reduced using a reducing agent such as sodium borohydride, sodium cyanoborohydride, lithium aluminum hydride or Red-Al to give the product, A—Y—B. The use of certain protecting groups and deprotection steps may be necessary, as will be appreciated by those skilled in the art.

Method 3

Amines of the general formula B, as defined above, can be coupled with the acid, A—W—CO$_2$H, wherein A and W are as defined above, using standard conditions such as 1-3-dicyclohexylcarbodiimide or 1-(3-dimethylaminopropyl)-3-ethylcarbodiimide and 1-hydroxybenzotriazole or 4-dimethylaminopyridine in a solvent such as dimethylformamide, acetonitrile, methylene chloride or a mixture thereof. The resulting amide can be reduced using a reducing agent such as lithium aluminum hydride, borane-dimethyl sulfide or Red-Al. The use of certain protecting groups and deprotection steps may be necessary, as will be appreciated by those skilled in the art.

Methods for synthesizing compounds of formula (I) are further illustrated by the following reaction schemes and written descriptions thereof:

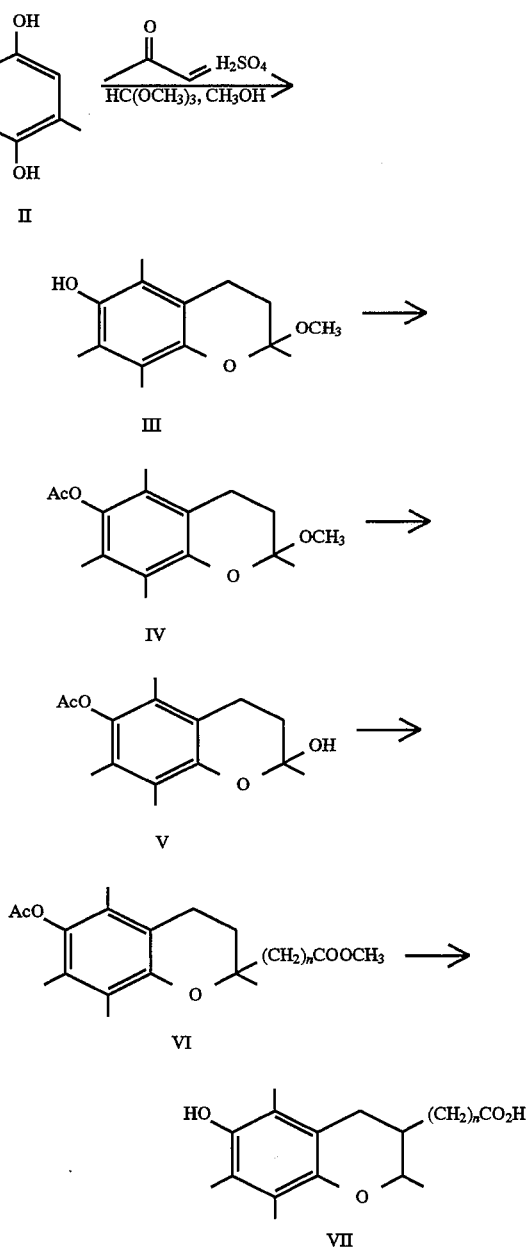

Scheme 1

Scheme 2
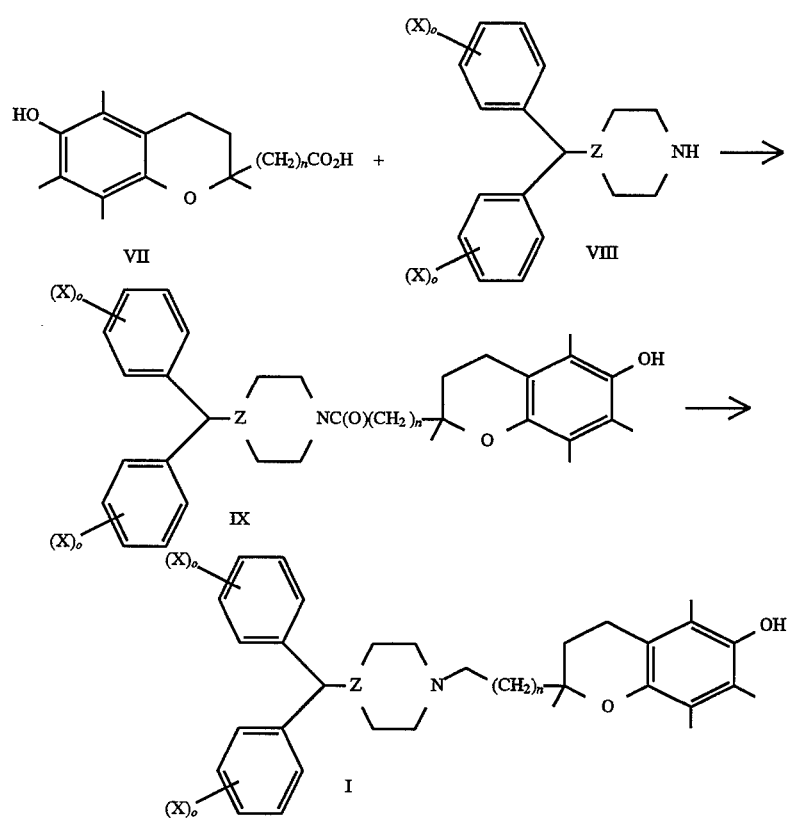
Scheme 3
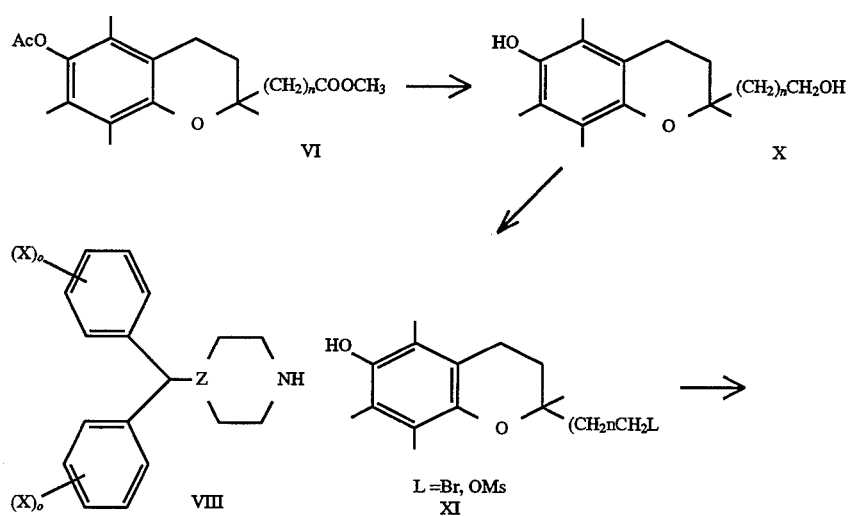

-continued
Scheme 3
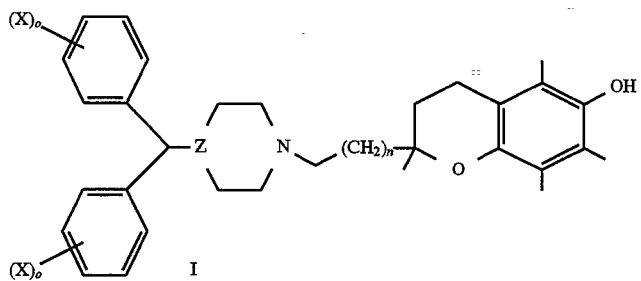
I
Scheme 4
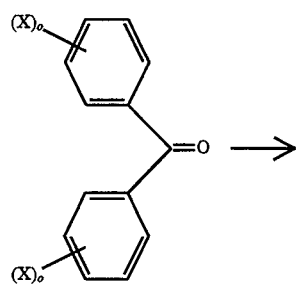
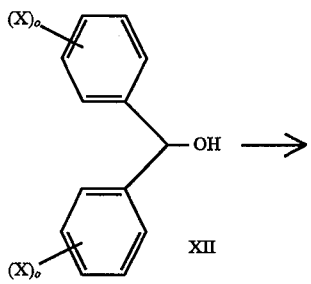
XII
-continued
Scheme 4
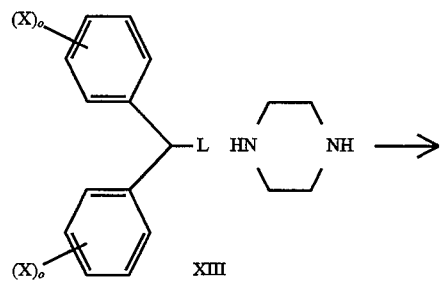
L = OMS, Cl, Br
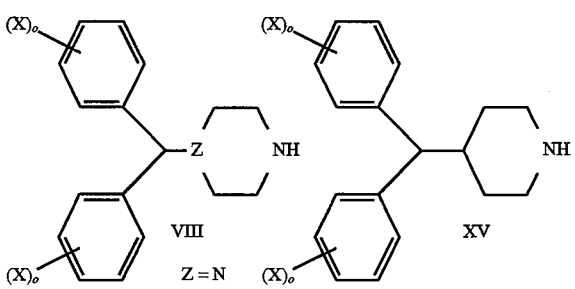
VIII    XV
Z = N
Scheme 5
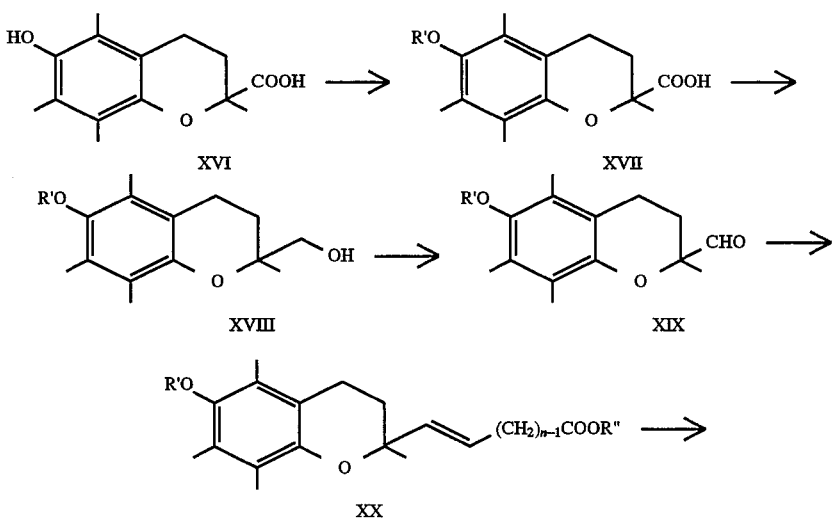

-continued
Scheme 5

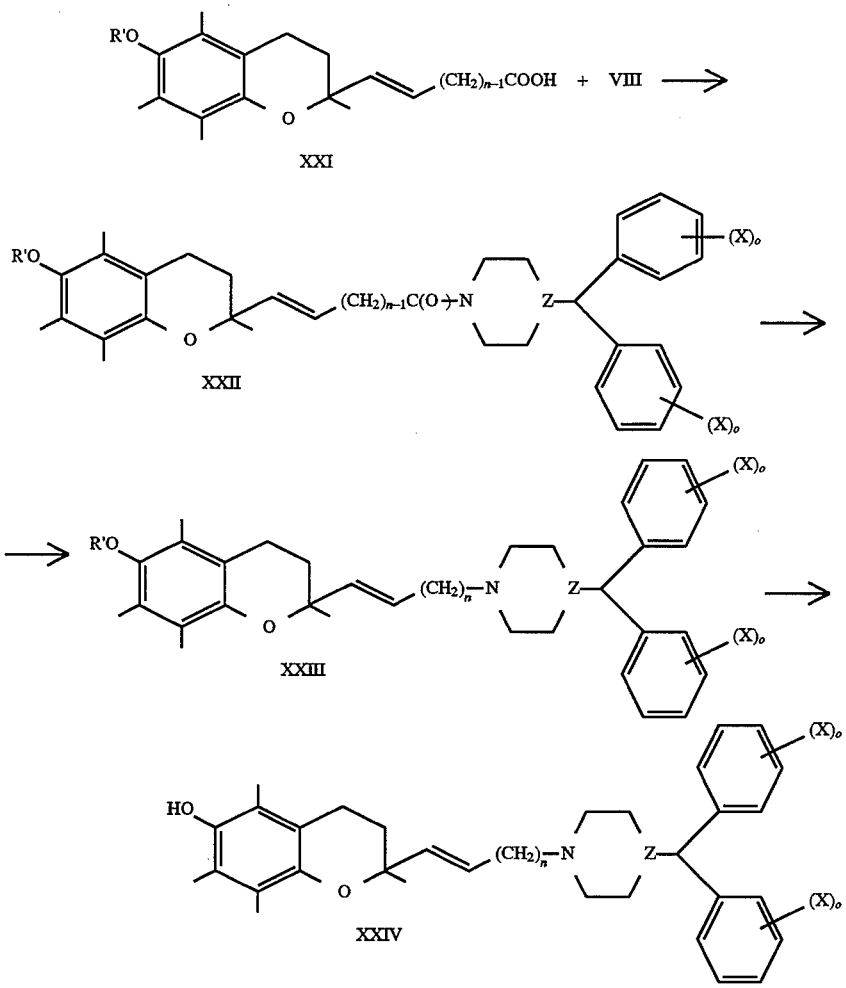

Using the general methods outlined in *J. Amer. Oil Chem. Soc.*, volume 51, pages 200–203 (1974), the hydroquinone (II, Scheme 1) is condensed with methyl vinyl ketone in the presence of triethyl orthoformate, methanol and acid to give the benzopyran derivative, III. Acetyladon (acetic arthydride, pyridine) and mild hydrolysis gave the hemiacetal, V. Reaction of the hemiketal, V, using a Wittig or Horner Emmons type reaction affords VI. Hydrolysis of the diester provides the phenol-carboxylic acid, VII. The compound, VII, where n=0 is commercially available from Aldrich Chemical Company, Milwaukee, Wis., U.S.A. ("Aldrich").

The carboxylic acid, VII, can be coupled to an appropriate amine (VIII) using standard methods (Scheme 2). The preferred methods include using 1-3-dicyclohexylcarbodiimide or 1-(3-dimethylaminopropyl)-3-ethylcarbodiimide and 1-hydroxybenzotriazole or 4-dimethyl aminopyridine in a solvent such as dimethylformamide, acetonitrile, methylene chloride or a mixture thereof. Reduction of the resulting amide (IX) (preferably using borane-dimethyl sulfide in tetrahydrofuran) provides compounds of formula (I). This is the preferred method of preparing compounds of formula (I).

Compounds of formula (I) may also be prepared as described in Scheme 3. Reduction of the diester, VI (preferably with lithium aluminum hydride) affords the phenol-alcohol, X. The alcohols may also be formed directly as described in European Patent Publication No. 0 369 082 A. Activation of the alkyl alcohol by conversion to the halide (by using triphenyl phosphine, bromine and carbon tetrachloride, for example) or an organic sulfonate (mesylate or tosylate) and reaction with the appropriate amine (VIII) using standard procedures results in the formation of compounds of formula (I). The standard procedures referred to in the preceding sentence involve the reaction of an equimolar quantity of the halide or sulfonate with an amine in an organic solvent, such as acetonitrile or dimethyl formamide, in the presence of a base, such as potassium carbonate or diisopropylethylamine typically, at temperatures between 20° and 120° C.

The appropriate amines (VIII, Z=N) are commercially available (e.g., 4,4'-difluorobenzhydryl piperazine is available from Spectrum Chemical Manufacturing Company, Gardena, Calif., U.S.A. ("Spectrum"), and diphenylbenzhydryl piperazine is available from Aldrich), or can be prepared by known methods (e.g., Scheme 4), using commercially available benzophenone derivatives. The benzophenones can be reduced to the benzhydryl derivatives, XII, by using sodium borohydride or catalytic hydrogenation, for example. Activation of the resulting alcohol by conversion to the halide (using thionyl chloride or methanesulfonyl chloride, for example) and then reaction with piperazine can provide the desired amine (I). The amines of formula XV can be prepared by one skilled in the art using methods described in the scientific literature, such as *J. Med. Chem.*, volume 34(10), pages 3011-3022 (1991), and references cited therein.

Compounds of the formula XXIV can be prepared by the route outlined in Scheme 5. The phenolic OH group can be protected by means of tert-butyldimethylsilyl ether or benzyl ether or similar groups in order to provide XVII. Reduction of the carboxylic acid (using lithium aluminum hydride, for example) provides the alcohol, XVIII. Oxidation of the alcohol (preferably using the Swern oxidation procedure: oxalyl chloride, dimethyl sulfoxide and triethylamine) provides the aldehyde, XIX. Wittig or Horner Emmons type reaction of the aldehyde provides the homologous ester. The ester can be hydrolyzed by using sodium hydroxide in a mixture of ethanol and water. The free carboxylic acid is coupled to the amine, XI, to give the amide XXII using standard methods. The preferred methods include using 1,3-dicyclohexylcarbodiimide or 1-(3-dimethylaminopropyl)-3-ethylcarbodiimide and 1-hydroxybenzotriazole or 4-dimethylaminopyridine in a solvent such as dimethylformamide, acetonitrile, methylene chloride or a mixture thereof. Reduction of the amide, preferably by adding a solution of lithium aluminum hydride in ether to a solution of the amide in tetrahydrofuran at temperatures between −78° and 23° C., can give the amine, XXIII. Deprotection of the phenolic oxygen under standard conditions, which may vary depending on the protecting group utilized, provides the amine XXIV.

The compounds of formula (XXVI), below, may be prepared by the route outlined in Scheme 6:

Scheme 6

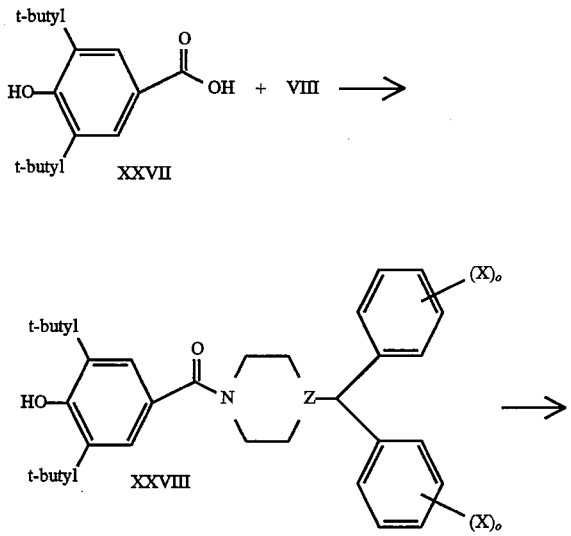

-continued
Scheme 6

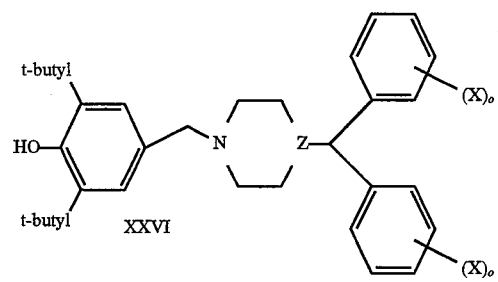

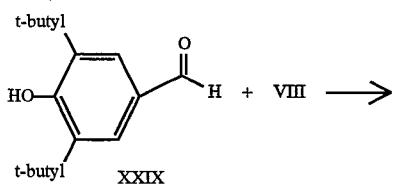

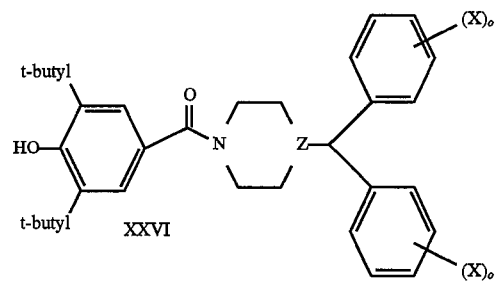

The carboxylic acid of formula (XXVII) which is commercially available (Aldrich) can be coupled to an appropriate amine (VIII) using standard methods. The preferred methods include using 1,3-dicyclohexylcarbodiimide or 1-(3-dimethylaminopropyl)-3-ethylcarbodiimide and 1-hydroxybenzothiazole or 4-dimethylaminopyridine in a solvent such as dimethylformamide, acetonitrile, methylene chloride or a mixture thereof. Reduction of the resulting amide (XXVIII), preferably using borane-dimethyl sulfide in tetrahydrofuran, provides compounds of formula (XXVI).

Alternatively, the compounds can be prepared by reacting the commercially available aldehyde (XXIX, Aldrich) with the appropriate amine (VIII) and then reducing the intermediate formed (Scheme 6). The reactants can be warmed (temperature 40°–120° C.) in a solvent, preferably toluene, for 12 to 35 h. The reaction mixture is concentrated and the residue can be dissolved in a solvent, most preferably anhydrous tetrahydrofuran. The intermediate can be reduced (using lithium aluminum hydride, for example) to give compounds of the formula (XXVI).

Compounds of formula (XXXII) and formula (XXXIII), below, can be prepared by the methods outlined in Scheme 7:

Scheme 7

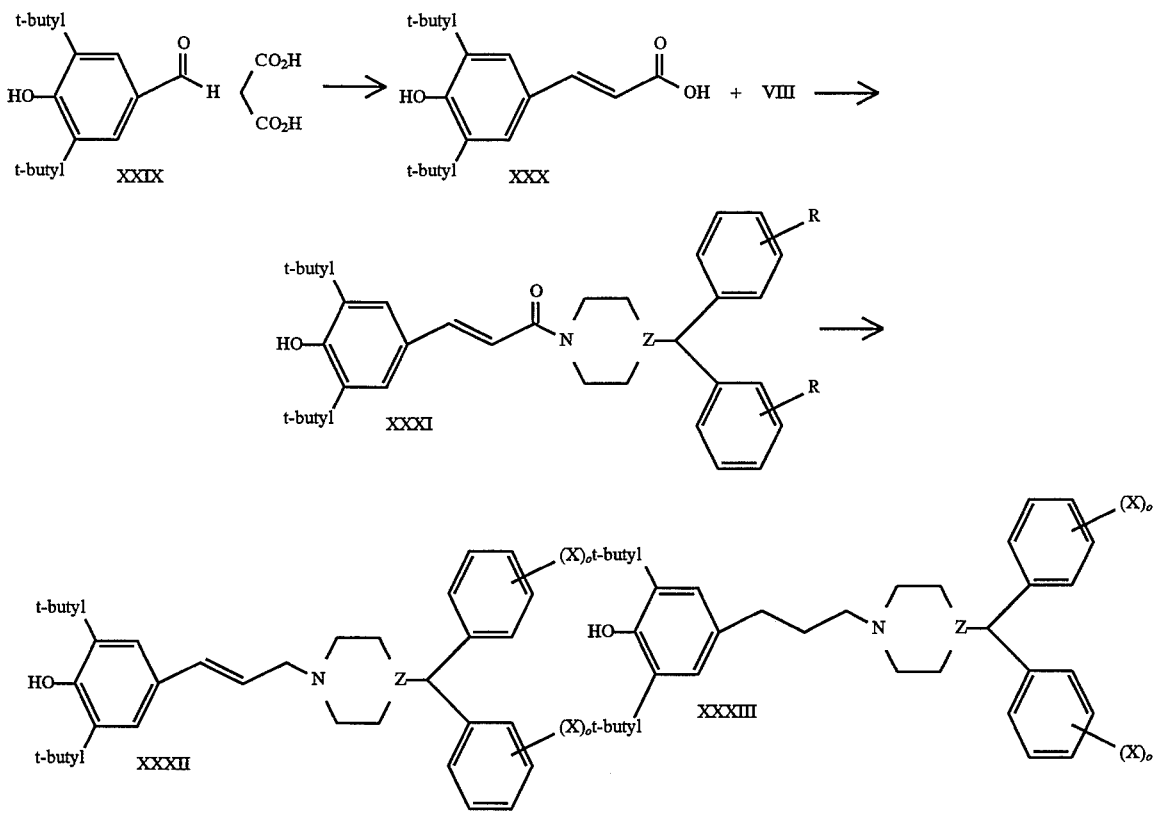

The commercially available benzaldehyde (XXIX, Aldrich) is reacted with malonic acid, and base (such as piperidine) and an acid (such as acetic acid) in an inert solvent (such as toluene). Removal of water generated during the reaction can be accomplished by using molecular sieves or most preferably a Dean Stark trap, as described in J. Med. Chem. volume 34, pages 518–525 (1991). The carboxylic acid (XXX) can be coupled to an appropriate amine (VIII) using standard methods. The preferred methods include using 1,3-dicyclohexylcarbodiimide or 1-(3-dimethylaminopropyl)-3-ethylcarbodiimide and 1-hydroxybenzotriazole or 4-dimethylaminopyridine in a solvent, such as dimethylformamide, acetonitrile, methylene chloride or a mixture thereof. The resulting amide (XXXI) is reduced by adding a solution of lithium aluminum hydride to a solution of the amide in a solvent, such as tetrahydrofuran, at temperatures between −78° to 20° C. to give compound XXXII. Reduction of the amide by adding a solution of the amide to a slurry of lithium aluminum hydride at −10° to 35° C. results in the formation of compound of the formula (XXXIII).

The compounds of formula (I) are typically converted to amine salts by reacting the amine with acids of sufficient strength to produce an organic or inorganic salt. The anions of the preferred pharmaceutically acceptable salts include acetate, bromide, chloride, citrate, maleate, fumurate, mesylate, phosphate, sulfate and tartarate.

Since there is an asymmetric carbon atom at the 2-position of the benzopyran ring, the compounds may occur as either the R or S enantiomers, or mixtures thereof. The preparation of the individual enantiomeric form may be effected by resolving the acids of formula (VII) by conventional means such as the use of diastereomeric salt with optically active amines. The alcohols of formula (XVIII) could be resolved by forming the esters with optically active carboxylic acids, carrying out the resolution and then hydrolyzing the resolved diastereomers.

The compounds of formula (I) may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. The ophthalmic compositions of the present invention will include one or more compounds of formula (I) and a pharmaceutically acceptable vehicle for said compound(s). Various types of vehicles may be utilized. The vehicles will generally be aqueous in nature. Aqueous solutions are generally preferred, based on ease of formulation, as well as patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for compounds of formula (I) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level of from 0.001% to 1.0% by weight.

Some of the compounds of formula (I) may have limited solubility in water and therefore may require a surfactant or other appropriate co-solvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 2% by weight.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The pharmaceutical compositions containing one or more compounds of formula (I) may be used to treat patients afflicted with or prone to various types of cellular damage. The concentrations of the compounds in the compositions will depend on various factors, including the nature of the condition to be treated with the compositions. However, the compositions will generally contain one or more of the compounds in a concentration of from about 0.001 to about 5 percent by weight, based on the total weight of the composition ("wt. %").

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formula (I) to prevent or reduce damage to ophthalmic tissues at the cellular level is a particularly important aspect of the present invention. Ophthalmic conditions which may be treated include, but are not limited to, cataracts, retinopathies, heredodegenerative diseases, macular degeneration, ocular ischemia, neovascular diseases, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compounds are administered incaocularly. As utilized herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., U.S.A.) are examples of physiologically balanced intraocular irrigating solutions. The latter type of solution is described in U.S. Pat. No. 4,550,022 (Garabedian, et al.), the entire contents of which are hereby incorporated in the present specification by reference.

The doses utilized for any of the above-described purposes will generally be from about 0.01 to about 100 milligrams per kilogram of body weight ("mg/kg"), administered one to four times per day.

The present invention is further illustrated by means of the following examples. Examples 1–5 illustrate the synthesis of compounds of formula (I); Example 6 demonstrates the physiological activity of the compounds, and methods for measuring that activity; and Example 7 further illustrates the pharmaceutical compositions of the present invention.

EXAMPLE 1

Preparation of 1-benzyhydryl-4-(6-hydroxy-2,5,7,8-tetramethylchroman-2-methyl)piperazine dihydrochloride (Compound No. 5)

A solution of dicyclohexyl carbodiimide (Aldrich, 4.90 g, 23.77 mmol) in methylene chloride (50 mL) was added dropwise over twenty minutes to a stirring solution of 1-(diphenylmethyl)piperazine (Spectrum, 5.00 g, 19.81 mmol), Trolox® (a registered trademark of Hoffman-LaRoche, Nutley, N.J., U.S.A., available from Aldrich, 4.96 g, 19.81 mmol) and 1-hydroxybenzotriazole hydrate (Aldrich, 3.20 g, 23.77 mmol) in methylene chloride (200 mL) which was cooled in an ice/water bath. After 1 h (note: the abbreviation "h" is used herein for the terms "hour" and "hours"), the temperance of the reaction mixture was allowed to warm to ambient temperature. After stirring at ambient overnight, the reaction mixture was filtered and the filtrate was washed with water (2×100 mL), dried (MgSO$_4$) and concentrated in vacuo. The residue was purified by chromatography (flash, silica gel, methylene chloride/methanol 98:2) to give 8.10 g of an oil that crystallized on standing. The solid was recrystallized from ethyl acetate/hexane to give 7.2 g (75% yield) of benzylhydryl 6-hydroxy-2,5,7,8-tetramethylchroman-2-formyl 4-(benzhydryl)piperazine as a white solid.

$^1$H NMR (CDCl$_3$) δ7.4–7.1 (m, 10H), 4.3 (s, 1H), 4.1 (s, 1H), 4.1–3.2 (m, 4H) 2.9–2.5 (m,4H), 2.1 (s, 3H), 2.0 (bs, 6H), 1.8–1.7 (m, 2H), 1.5 (s, 3H). IR (KBr) v3421 (bs, 2928 (s), 1596 (s), 1453 (s), 1241 (s), 1214 (s), 1189 (s), 1116 (s), 1097 (s) cm$^{-1}$.

Mass Specimen: m/e 485 (M$^+$+1, 100), 209, 167.

Elemental Analysis: Calculated for C$_{31}$H$_{36}$N$_2$O$_3$. Calculated: C, 76.82; H, 7.49; N, 5.78 Found: C, 76.87; H, 7.46; N, 5.76

Melting Point: 133°–135° C.

A solution of borane-dimethyl sulfide in tetrahydrofuran (Aldrich 2M, 25.8 mL, 51.69 mmol) was added dropwise to a stirring solution of benzhydryl 6-hydroxy-2,5,7,8-tetramethychroman-2-formyl 4-(benzhydryl)piperazine (8.35 g, 17.23 mmol) in tetrahydrofuran. When the addition was complete, the reaction mixture was warmed at reflux. Dimethyl sulfide and tetrahydrofuran were removed using a Dean-Stark trap. The reaction mixture warmed at reflux for 6 h and then allowed to stir at ambient temperature for 14 h. The reaction mixture was cooled in an ice/water bath and concentrated hydrochloric acid was added dropwise with caution. When the addition was complete, the reaction mixture was warmed at reflux for 1 h. The reaction mixture was cooled to ambient temperature and added to 300 mL of water. The resulting slurry was extracted with methylene chloride (3×200 mL). The combined organics were washed with water (200 mL), dried (MgSO$_4$) and concentrated in vacuo. The residue was purified by chromatography (flash, silica gel, ethyl acetate/hexane 3:7) to give 7.2 g 88.8% yield) of the free base as an oil. A 2.5 g sample of the free base was dissolved in an ethanol/ether mixture and the resulting mixture was filtered. The filtrate was treated with ethereal hydrogen chloride (Aldrich, 2M) and the resulting solution was allowed to stand at ambient temperature overnight. The white solid that formed was collected by filtration to give 2.19 g (81% yield, 71% overall yield for the reduction) of Compound No. 5 as a white solid.

$^1$H NMR (d$_6$-DMSO) δ8.1–7.2 (bm, 10H), 4.0–3.2 (m, 10H), 3.38 (q, 2H ethanol), 2.7–2.5 (m, 4H), 2.03 (s, 3H), 2.01 (s, 3H), 1.96 (s, 3H), 1.9–1.8 (m, 2H), 1.2 (s, 3H), 1.0 (, 3H ethanol).

IR (KBr) ν3388 (s), 2930 (s), 2495 (s), 2421 (s), 1455 (s), 1381 (s), 1259 (s), 1113 (s), 1089 (s).

Mass Spectrum: m/e 471 (M$^+$+1, 100), 393, 265.

Elemental Analysis: Calculated for C$_{33}$H$_{38}$N$_2$O$_3$·2HCl·EtOH Calculated: C, 67.22; H, 7.68; N, 4.75. Found: C, 67.41; H, 7.96; N, 4.67.

Melting Point: 210°–212° C.

EXAMPLE 2

Preparation of (4-(4,4'-difluorobenzhydryl) piperazine)-3-(4-hydroxy-3,5-bis(1,1-dimethylethyl) phenyl)-2-propene dimaleate (Compound No. 6)

A solution of malonic acid (Aldrich, 4.36 g, 41.9 mmol), 3,5-di-tert-butyl-4-hydroxybenzaldehyde (Aldrich, 5.00 g, 20.9 mmol), piperidine (Aldrich, 0.18 g, 2.10 mmol) and acetic acid (0.13 g, 2.10 mmol) in toluene (100 mL) was warmed at reflux (water removed using a Dean-Stark trap). After 5.5 h malonic acid was added (4.36 g, 41.9 mmol) and the reaction mixture was warmed at reflux for 12 h. The reaction mixture was cooled to ambient temperature and concentrated in vacuo. The residue was chromatographed (SiO$_2$, flash, methanol-methylene chloride, 5:95) to give 2.43 g (42.1% yield of (E)-1-(3,5-bis(1,1-dimethylethyl)-4-hydroxyphenyl propenoic acid as a white solid.

$^1$H NMR (CDCl$_3$) δ8.0 (d, 1H), 7.4 (s, 2H), 6.3 (d, 1H), 5.6 (bs, 1H), 1.46 (s, 18H), Mass Spectra: m/e 277 (M$^+$+1, 100).

A solution of dicyclohexylcarbodiimide (Aldrich, 2.35 g, 11.4 mmol) in methylene chloride (40 mL) was added to a solution of 4,4-difluorobenzhydrylpiperazine (Schweizerhall, Inc., South Plainfield, N.J., U.S.A., referred to herein as "Schweizerhall") 1.45 g, 5.02 mmol), (E)-1-(3, 5-bis(1,1-dimethylethyl)-4-hydroxyphenyl propenoic acid (2.43 g, 8.79 mmol) and 1-hydroxybenzotriazole hydrate (Aldrich, 1.54 g, 11.4 mmol) which had been stirred for 10 min. The reaction mixture was stirred for 24 h and then was filtered. The filtrate was concentrated in vacuo and the residue was chromatographed (SiO$_2$, flash, methanol methylene chloride, 1:99). The solid that formed upon the concentration of the appropriate fractions was recrystallized from ethyl acetate to give 1.65 g (60.2% yield of 3-(4-hydroxy-3,5-bis(1,1-dimethylethyl)propenoyl 4-(4,4'-difluorobenzhydryl)piperazine as a white solid, melting point 240°–242° C.

$^1$H NMR (CDCl$_3$) δ7.6 (d, 1H), 7.4 (m, 4H), 7.3 (s, 2H), 7.0 (m, 4H), 6.7 (d, 1H), 5.5 (s, 1H), 4.3 (bs, 1H), 3.7 (m, 4H), 2.4 (m, 4H), 1.5 (s, 18H).

IR (KBr) ν3450.5, 2960.9, 1642.4, 1597.6, 1505.4, 1436.9, 1222.2, 1099.7 cm$^{-1}$.

Mass Spectra: m/e 547 (M$^+$+1, 100), 203.

Elemental Analysis: Calculated for C$_{34}$H$_{40}$N$_2$O$_2$F$_2$ Calculated: C, 76.69; H, 7.38; N, 5.12 Found: C, 74.63; H, 7.36; N, 5.15

Melting Point: 240°–242° C.

A solution of 3-(4-hydroxy-3,5-bis(1,1-dimethylethyl) propenoyl 4-(4,4'-difluorobenzhydryl)piperazine (7.40 g, 13.53 mmol) in tetrahydrofuran (100 mL) was cooled to −70° C. A solution of lithium aluminum hydride in diethyl ether (Aldrich, 1M, 14.9 mL, 14.9 mmol) was added dropwise over five minutes. After the addition was complete the reaction mixture was stirred at −75° C. for 2 h. The solution was then allowed to come to ambient temperature and was stirred at ambient temperature for 4 h. The reaction mixture was cooled in a water/ice bath and was quenched by the sequential addition of 5 mL of 10% aqueous tetrahydrofuran, 0.5 mL of 15% aqueous sodium hydroxide and 1.5 mL of water. The mixture was stirred for thirty minutes, filtered through a Celite™ filtering pad (Johns-Manville Corporation) and concentrated in vacuo. The residue was partitioned between water (100 mL) and methylene chloride (100 mL). The layers were separated and the organic layer was dried (MgSO$_4$) and concentrated in vacuo. The residue was purified by flash chromatography on silica gel (99:1 methylene chloride:methanol) to give 2.50 g (36.0%) of the free base as an oil.

The oil was dissolved in ethanol and treated with a solution of maleic acid (1.24 g, 10.7 mmol) in ethanol. The solid that formed was collected by filtration and recrystallized from ethanol to afford 1.40 g of Compound No. 6 as an off-white powder, melting point 182°–186° C.

$^1$H NMR (d$_6$-DMSO) δ7.4 (dd, 4H), 7.1 (dd, 4H), 6.7 (d, 2H), 6.1 (s, 4H), 4.5 (s, 1H), 3.8 (bd, 2H), 3.5–2.1 (bm, 8H), 1.4 (s, 18H).

IR (KBr) ν3640 (m), 3433 (bm), 3044 (s), 2956 (bm), 1702 (s), 1619 (s), 1573 (s), 1511 (s), 1469 (s), 1384 (s), 1355 (s), 1308 (s), 1233 (s), 1161 (s), 1080 (s) cm$^{-1}$.

Mass Spectrum: m/e 533 (M$^+$+1, 100), 329, 301, 289

Elemental Analysis: Calculated for C$_{42}$H$_{50}$N$_2$O$_9$F$_2$ Calculated for: C, 65.95; H, 6.59; N, 3.66 Found: C, 65.70; H, 6.70; N, 3.59

Melting Point: 182°–186° C.

EXAMPLE 3

Preparation of 1-(4,4'-difluorobenzhydryl-4-(3,5-bis (1,1-dimethylethyl)-4-hydroxyphenyl)methyl) piperazine dimaleate monohydrate (Compound No. 7)

A mixture of 4,4'difluorobenzhydryl piperazine (Schweizerhall, 2.00 g, 6.93 mmol) and 3,5-di-tert-butyl-4- hydroxybenzaldehyde (Aldrich, 1.62 g, 6.93 mmol) in toluene (100 mL) was warmed at reflux in a 250 mL round bottom flask equipped with a Dean-Stark trap to facilitate the removal of water. After warming at reflux for 27 h, the reaction mixture was concentrated in vacuo. The residue was dissolved in tetrahydrofuran (50 mL) and the resulting solution was added dropwise to a stirring slurry of lithium aluminum hydride (Aldrich, 0.52 g, 13.86 mmol) which was cooled by an ice/water bath. After the addition was complete the reaction was stirred for 1 h. The reaction was quenched by the sequential addition of an aqueous solution of tetrahydrofuran (5% water in tetrahydrofuran, 10 mL), 50% aqueous sodium hydroxide (0.5 mL) and water (1.5 mL). The reaction mixture was filtered through a Celite™ filtering pad and the filtrate was concentrated in vacuo. The residue was partitioned between water (50 mL) and methylene chloride (100 mL). The layers were separated and the organic layer was washed with water (50 mL), dried (MgSO$_4$) and concentrated in vacuo.

The resulting oil was chromatographed (flash, SiO$_2$, Merck, 9:0.2 methylene chloride/methanol) to give 2.38 g of the desired amine.

The amine was dissolved in 30 mL of ethyl acetate and this solution was added to a solution of maleic acid (Aldrich, 1.33 g, 11.5 mmol) in ethyl acetate (30 mL). A solid formed and was collected by filtration. Recrystallized from ethyl acetate afforded Compound No. 7 (1.59 g, 31.0% yield) as a white solid, melting point 140°–143° C.

$^1$H NMR (d$_6$-DMSO, 200 mHz) δ11.0 (bs, 2H), 7.4 (m, 4H), 7.2 (m, 6H), 6.1 (s, 4H), 4.6 (s, 1H), 4.2 (s, 1H), 3.4–3.0 (m, 8H), 3.0–2.8 (m, 2H), 2.2 (m, 2H), 1.4 (s, 18H),

IR (KBr) ν3629.9, 3568.2, 3428.2, 2960.5, 1710.7, 1605.7, 1580.0, 1510.0, 1472.0, 1391.5, 1353.2, 1236.9, 1163.6, 1122.5, 1096.2 cm$^{-1}$.

Mass Spectrum: m/e 507 (M$^+$+1), 301, 289, 219, 117 (100).

Elemental Analysis: Calculated for C$_{32}$H$_{40}$N$_2$OF$_2$·2C$_4$H$_4$O$_4$·H$_2$O Calculated: C, 63.48; H, 6.66; N, 3.70 Found: C, 63.50; H, 6.57; N, 3.65

Melting Point: 140°–143° C.

EXAMPLE 4

Preparation of 1-(4,4'-difluorobenzhydryl)-4-(6-hydroxy-2,5,6,8-tetramethylchroman-2-methyl) piperazine dimaleate hemihydrate (Compound No. 2)

A solution of 1,3-dicyclohexylcarbodiimide (Aldrich, 6.81 g, 23.62 mmol) in methylene chloride (20 mL) was added to a stirred slurry of Trolox® (10.00 g, 39.95 mmol), 4,4'difluorobenzhydrylpiperazine (Schweizerhall, 11.52 g, 39.95 mmol) and 1-hydroxybenzotriazole hydrate (Aldrich, 7.02 g, 51.94 mmol) in methylene chloride (160 mL) which was cooled by an ice/water bath. After five minutes, an additional solution of 1,3-dicyclohexylcarbodiimide (Aldrich, 3.90 g, 13.54 mmol) in methylene chloride was added. After 3 h, the reaction mixture was allowed to warm to ambient temperature. After stirring at ambient temperature for 3.5 h, the reaction mixture was filtered. The filtrate was washed with water (2×100 mL), dried (MgSO$_4$) and concentrated in vacuo. The resulting residue was chromatographed (flash, silica gel, Merck, 99:1 to 95:5, methylene chloride to methanol) to give 6.42 g of the desired amide (31.0% yield).

A 2.4 g sample was dissolved in methylene chloride (200 mL) and 100 mL of 3.7% aqueous hydrochloric acid was added. A solid formed which was collected by filtration. The solid was recrystallized from ethanol to afford 1.78 g (76.8%) of 6-hydroxy-2,5,7,8-tetramethylchroman-2-formyl 4-(4,4'-difluorobenzhydryl)piperazine as a whim solid, melting point 220° C., decomposing at 223° C.

$^1$H NMR (d$_6$-DMSO, 200 mHz) δ12.7 (s, 1H), 7.9 (m, 4H), 7.3 (m, 4H), 5.7 (s, 1H), 5.0–3.0 (m, 12H), 2.5 (m, 3H), 2.0 (s, 3H), 1.9 (s, 3H), 1.5 (bs, 3H).

IR (KRr) ν3385.5, 3065.4, 2993.7, 2370.4, 1606.2, 1241.5, 1189.2, 1164.3, 1103.9, 1089.5 cm$^{-1}$.

Mass Spectrum: m/e 521 (M$^+$+1, 100), 245, 203

Elemental Analysis: Calculated for: C$_{31}$H$_{34}$N$_2$O$_3$F$_2$—HCl Calculated: C, 66.83; H, 6.33; N, 5.02 Found: C, 66.47; H, 6.20; N, 4.95

Melting Point: 220° C., decomposed 223° C.

A solution of 6-hydroxy-2,5,7,8-tetramethylchroman-2-formyl 4-(4,4'-difluorobenzhydryl)piperazine (3.91 g, 7.51 mmol) in anhydrous tetrahydrofuran was added dropwise to a stirring solution of borane/dimethyl sulfide (Aldrich, 2M in THF, 16.33 mL, 332.67 mmol). After the addition was complete, the reaction mixture was warmed at reflux. Dimethyl sulfide was collected in a Dean-Stark trap. After the reaction mixture warmed at reflux for 6 h, it was allowed to cool to ambient temperature. Concentrated hydrochloric acid (21.6 mL) was cautiously added dropwise and the reaction mixture was warmed at reflux for 0.5 h. After cooling to ambient temperature, the reaction mixture was added to a mixture of water (400 mL) and methylene chloride (100 mL). The pH of this mixture was adjusted to 7–8 with 50% aqueous sodium hydroxide. The layers were separated and the aqueous layer was extracted with methylene chloride (2×100 mL). The combined organic extracts were washed with saturated aqueous sodium chloride (100 mL), dried (MgSO$_4$) and concentrated in vacuo. The residue was chromatographed (flash, 200 g, SiO$_2$, 8:2, hexane to ethyl acetate) to give 3.18 g (83.7%) of the desired amine. The amine as dissolved in 50 mL of ethyl acetate and this solution was added to a solution of maleic acid (Aldrich, 1.60 g, 13.8 mmol) in ethyl acetate. A solid formed and was collected by filtration. Recrystallization of this solid from ethyl acetate gave 2.51 g (46.2%) of Compound No. 2 as a yellow solid, melting point 95°–100° C.

$^1$H NMR (d$_6$-DMSO, 200 mHz) δ11.0 (bs, 2H), 7.5 (m, 4H), 7.1 (m, 4H), 6.1 (s, 4H), 4.6 (s, 1H), 3.3 (m, 10H), 2.6 (m, 2H), 2.1 (s, 3H), 2.0 (d, 3H), 1.9 (s, 3H), 1.8 (m, 2H), 1.2 (s, 3H).

IR (KBr) ν3420.6, 2938.8, 2570.7, 1909.1, 1711.4, 1584.2, 1501.7, 1363.1, 1230.8, 1084.5 cm$^{-1}$.

Mass Spectrum: m/e 507 (M$^+$+1, 100), 203.

Elemental Analysis: Calculated for: C$_{31}$H$_{36}$N$_2$O$_2$F$_2$·2C$_4$H$_4$O$_4$·5 H$_2$O Calculated: C, 62.63; H, 6.07; N, 3.74 Found: C, 62.64; H, 6.12; N, 3.74

Melting Point: 95°–100° C.

EXAMPLE 5

Preparation of 1-(4,4'-difluorobenzhydryl)-4-(6-hydroxy-2,5,7,8-tetramethylchroman-2-ethyl) piperazine (Compound No. 1)

This compound was prepared by means of a multiple-step synthesis as described below.

Preparation of 6-hydroxy-2-methoxy-2,5,7,8-tetramethylchroman.

Concentrated sulfuric acid (0.8 mL) was added dropwise to a solution of trimethyl orthoformate (Aldrich, 48.5 g, 457.0 mmol) and trimethyl hydroquinone (Aldrich, 50.0 g, 328.5 mol) in methanol (200 mL), cooled by a water/ice bath. Methyl vinyl ketone (Aldrich, 46.05 g, 657.0 mmol) was added slowly (1.5 h) to the reaction mixture while the reaction mixture was cooled by an ice/water bath. A pasty slurry formed. The reaction mixture was allowed to come to ambient temperature and was stirred at ambient temperature for 48 h. The reaction mixture was diluted with diethyl ether (600 mL) and the resulting solution was extracted with water (2×200 mL) and saturated aqueous sodium bicarbonate (2×100 mL). The organic solution was dried (sodium sulfate) and concentrated in vacuo to give a tan solid. The solid was recrystallized from methanol to give 71.8 g (92.6%) of the desired product as a tan solid.

$^1$H NMR (CDCl$_3$, 200 mHz) δ4.3 (s, 1H), 3.2 (s, 3H), 2.9–2.5 (m, 2H), 2.15 (s, 3H), 2.14 (s, 3H), 2.11 (s, 3H), 1.9–1.7 (m, 2H), 1.5 (s, 3H).

Preparation of 6-acetoxy-2-methoxy-2,5,7,8-tetramethylchroman.

Acetic anhydride (135 mL) was added dropwise to a solution of 6-hydroxy-2-methoxy-2,5,7,8-tetramethylchroman (71.8 g, 303.85 mmol) in pyridine (90 mL) which was cooled by an ice/water bath. After the addition was complete, the reaction mixture was allowed to warm to ambient temperature. After stirring at ambient temperature for 18 h, the reaction mixture was added to 1 L of ice water. This mixture was allowed to stir for 2 h and was then extracted with diethyl ether (3×200 mL). The combined organics were washed with 2N HCl (200 mL), brine (200 mL), saturated sodium bicarbonate (200 mL) and brine (200 mL). The organic solution was dried (sodium sulfate) and concentrated in vacuo to give 74.11 g (87% crude yield) of a yellow solid which was used crude in the next reaction.

$^1$H NMR (CDCl$_3$) δ3.2 (s, 3H), 2.8–2.5 (m, 2H), 2.3 (s, 3H), 2.1 (s, 3H), 2.0 (s, 3H), 1.9 (s, 3H), 1.9–1.7 (m, 2H), 1.6 (s, 3H).

Mass Spectrum: m/e 278 (M$^+$+1), 247 (m/z), 236.

Preparation of 6-acetoxy-2-hydroxy-2,5,7,8-tetramethylchroman.

A solution of 6-acetoxy-2-methoxy-2,5,7,8-tetramethylchroman (74.11 g, 266.25 mmol), and concentrated sulfuric acid (2.5 mL) in a mixture of acetone (375 mL) and water 300 mL) was added to a distillation apparatus and warmed at reflux. Distillant was collected until the still head temperature reached 92° C. (about 1.5 h). The slurry was allowed to cool to 70° C. and 240 mL of acetone was added. The resulting mixture was allowed to cool to ambient temperature and the solid that formed was collected filtration. The solid was recrystallized from acetone and dried in a vacuum oven at 60° C. to afford 53.9 g (76.7% yield) of the desired product as a tan solid.

$^1$H NMR (CDCl$_3$) δ2.8 (bs, 1H), 2.8–2.5 (m, 2H), 2.3 (s, 3H), 2.1 (s, 3H), 2.0 (s, 3H), 1.98 (s, 3H), 1.9–1.7 (m, 2H), 1.6 (s, 3H).

Mass Spectrum: m/e 265 (M$^+$+1), 247 (m/z), 222, 205, 177.

Preparation of ethyl 6-acetoxy-2,5,7,8-tetramethylchroman-2-acetate.

A solution of triethyl phosphonoacetate (Aldrich, 33.91 g, 151.3 mmol) in tetrahydrofuran (150 mL) was added dropwise to a stirring slurry of sodium hydride (Aldrich, 60% oil suspension, 6.05 g, 151.3 mmol, washed with hexane (3×30 mL)) which was cooled by an ice/water bath. After the addition was complete, the reaction mixture was stirred at ambient temperature for 1 h. A solution of 6-acetoxy-2-hydroxy-2,5,7,8-tetramethylchroman (20.00 g, 151.3 mmol) in tetrahydrofuran (150 mL) was added dropwise at ambient temperature. After the reaction mixture stirred at ambient temperature for 18 h, it was heated at reflux for 4 h. The reaction mixture was cooled to ambient temperature and water (200 mL) was added. This mixture was concentrated in vacuo (removal of tetrahydrofuran) and the residue was extracted with diethyl ether (3×200 mL). The combined organic extracts were washed with water (200 mL) dried (sodium sulfate) and concentrated in vacuo to give 27.6 g (>100% crude yield) of the desired product as a brown oil that was used without further purification.

$^1$H NMR (CDCl$_3$) δ4.1 (q, 2H), 2.7–2.5 (m, 5H), 2.3 (s, 3H), 2.1 (s, 3H), 2.0 (s, 3H), 2.0 (s, 3H), 1.9 (s, 3H), 1.9–1.8 (m, 2H), 1.4 (s, 3H), 1.3 (t, 3H).

Mass Spectrum: m/e 335 (M$^+$+1, 100), 293, 289, 225.

Preparation of 6-hydroxy-2,5,7,8-tetramethylchroman-2-acetic acid.

A solution of ethyl 6-acetoxy-2,5,7,8-tetramethylchroman-2-acetate (36.5 g, ~108 mmol) and 50% aqueous sodium hydroxide (110 mL) in a mixture of ethanol (500 mL) and water (500 mL) was stirred at ambient temperature for 7 h. The reaction mixture was extracted with hexane (2×200 mL). The pH of the resulting solution was adjusted to ~2 with concentrated hydrochloric acid. Water (~200 mL) was added and the reaction mixture was cooled in an ice/water bath. Crystallization was induced by scratching with a glass rod and the solid that formed was collected by filtration. The solid was recrystallized from an ethanol/water mixture to give 20.2 g (70.9% yield) of the desired product as a tan solid.

$^1$H NMR (CDCl$_3$+d$_6$-DMSO) δ7.7 (bs, 2H), 2.7–2.5 (m, 4H), 2.14 (s, 3H), 2.10 (s,3H), 2.06 (s, 3H), 2.0–1.8 (m, 2H), 1.4 (s, 3H).

Mass Spectrum: m/e 264 (M$^+$+1, 100), 230, 164.

Preparation of 6-hydroxy-2,5,7,8-tetramethylchroman-2-acetyl 4-(4,4'difluorobenzhydryl)piperazine.

A solution of dicyclohexyl carbodiimide (Aldrich, 3.55 g, 17.23 mmol) in methylene chloride (50 mL) was added dropwise to a slurry comprised of 6-hydroxy-2,5,7,8-tetramethylchroman-2-acetic acid (4.14 g, 15.66 mmol), 4,4'-difluorobenzhydryl piperazine (Schweizerhall, 4.51 g, 15.66 mmol), and 1-hydroxybenzotriazole hydrate (Aldrich, 2.33 g, 17.23 mmol) in methylene chloride (150 mL) which was cooled by an ice/water bath. After the addition was complete, the reaction mixture was allowed to come to ambient temperature and was stirred at ambient temperature for 12 h. The reaction was filtered and the filtrate was concentrated in vacuo. The residue was chromatographed (flash, silica gel, 95:5 methylene chloride/methanol) to give an oil which crystallized from a mixture of ethyl acetate and hexane. The solid was crystallized from ethanol to give 3.67 g (43.8% yield) of the desired product as a white solid.

$^1$H NMR (CDCl$_3$) δ7.3 (m, 4H), 6.9 (m, 4H), 4.1 (s, 1H), 3.9–3.5 (m, 4H), 2.8–2.6 (m, 4H), 2.5–2.3 (m, 4H), 2.15 (s, 3H), 2.10 (s, 3H), 2.0 (s, 3H), 2.0–1.8 (m, 2H), 1.3 (s, 3H).

IR (KBr) v3400 (bs), 1621 (s), 1505 (s), 1419 (s), 1262 (s), 1218 (s), 1204 (s), 1089 (s).

Mass Spectrum: m/e 535 (M$^+$+1, 100), 331, 245, 203.

Elemental Analysis: Calculated for C$_{32}$H$_{36}$N$_2$O$_3$F$_2$ Calculated: C, 71.88; H, 6.79; N, 5.24. Found: C, 71.73; H, 6.81; N, 5.26.

Melting Point: 208°–210° C.

Preparation of 1-(4,4'-difluorobenzhydryl)-4-(6-hydroxy-2,5,7,8-tetramethylchroman-2-ethyl)piperazi A solution of borane:dimethylsulfide (Aldrich, 10.5M, 2.37 mL, 23.66 mmol) in tetrahydrofuran (25 mL) was added dropwise to a solution of 6-hydroxy-2,5,7,8-tetramethylchroman-2-acetyl 4-(4,4'difluorobehzhydryl)

piperazine (2.53 g, 4.73 mmol) in tetrahydrofuran (75 mL). After the addition was complete, the reaction mixture was warmed at reflux. A Dean-Stark trap was used to collect dimethyl sulfide and tetrahydrofuran. After warming at reflux for 3 h, the reaction mixture was stirred at ambient temperature for 12 h. Concentrated hydrochloric acid (2.3 mL) was cautiously added and the reaction mixture was warmed at reflux for 1.5 h. The reaction mixture was allowed to cool to ambient temperature and water was added (100 mL). The pH of the resulting mixture was adjusted to 7 with 1N sodium hydroxide. The aqueous solution was extracted with methylene chloride (3×100 mL). The combined organics were washed with brine, and water, dried (magnesium sulfate) and concentrated in vacuo. The residue was chromatographed (flash, silica gel, methylene chloride/methanol 95:5) to give 2.3 g of an off-white foam. A 1.5 g sample of the foam was chromatographed (flash, silica gel, ethyl acetate/hexane 1:1) to give 0.55 g (1.0 mmol) of the free base. The free base was dissolved in ethyl acetate and treated with a solution of maleic acid (0.27 g, 2.3 mmol) in ethyl acetate. The solid that formed was collected by filtration to give 0.8 g (34% yield) of Compound No. 1 as a white solid.

$^1$H NMR (d$_6$-DMSO) δ7.4 (m, 4H), 7.1 (m, 4H), 6.2 (s, 6H), 4.5 (bs, 1H), 3.6–3.0 (m, 8H), 2.8–2.6 (m, 2H), 2.3–2.1 (m, 2H), 2.03 (s, 3H), 1.99 (s, 3H), 1.9 (s, 3H), 1.9–1.7 (m, 2H), 1.2 (s, 3H).

IR (KBr) ν3427 (bs), 2935 (s), 2569 (s), 1727 (s), 1694 (s), 1607 (s), 1235 (s), 1192 (s), 1162 (s), 864 (s).

Mass Spectrum: m/e 521 (M$^+$+1), 117 (100).

Elemental Analysis: Calculated for: C$_{32}$H$_{38}$N$_2$O$_2$F$_2$·3C$_4$H$_4$O$_4$ Calculated: C, 60.82; H, 5.57; N, 3.22. Found: C, 60.81; H, 5.86; N, 3.23.

Melting Point: 137°–140° C.
Preparation of 1-(4,4'-difluorobenzhydryl)-4-(6-hydroxy-2,5,7,8-tetramethylchroman-2-ethyl)piperazine dihydrochloride hemihydate.

A solution of HCl in ether (Aldrich, 1M) was added to a solution comprised of the free base from Compound No. 1 (1.8 g, 3.46 mmol) in ether (50 mL). A white solid formed and was collected by filtration to give 1.77 g (85% yield) of the hemihydrate as a white solid.

$^1$H NMR (d$_6$-DMSO) δ7.5–7.4 (m, 4H), 7.2–7.1 (m, 4H), 4.7 (s, 1H), 4.3–2.8 (bm, 15H), 2.0 (s, 3H), 1.97 (s, 3H), 1.95 (s, 3H), 2.0–1.8 (m, 2H), 1.75 (t, 2H), 1.15 (s, 3H),

Mass Spectrum: 521 (M$^+$+1, 100), 319, 203.

Elemental Analysis: Calculated for: C$_{32}$H$_{38}$N$_2$O$_2$·2HCl·5 H$_2$O Calculated: C, 63.78; H, 6.86; N, 4.65. Found: C, 64.06; H, 7.06; N, 4.65.

EXAMPLE 6

Activity

The data presented in the following table demonstrate the calcium antagonist and antioxidant activities of the compounds of the present invention, relative to known compounds.

Summary of Activity

| Compound | DPPH % quench | Retinal Pieces IC50 µM | Liver Microsomes IC50 µM | Phospholipid Oxidation IC50 µM | Ca+2 Binding IC50 µM |
|---|---|---|---|---|---|
| Compound No. 1 | 99 | 0.01 | 1.0 | 3.6 | 1–10 |
| Compound No. 2 | 96 | 0.05 | ND | ND | 1–10 |
| BHT | 64 | 0.5 | 1.1 | 201. | ND |
| Vitamin E | 87 | 0.001 | 37 | 4.2 | ND |
| Flunarizine | ND | ND | 27.1 | 149 | 1–10 |

ND = not determined

The DPPH assay is a chemical assay used to determine free radical scavenging activity. The retinal pieces, liver microsomes and phospholipid oxidation models measure antioxidant activity. The calcium binding assay is a measure of the affinity of the compound for a calcium antagonist binding site. The test procedures are described in greater detail below.

Free radical scavenging activity was determined by measuring the test compound's ability to quench a ethanol solution of the free radical dye, 1,1-diphenyl-2-picrylhydrazyl, (DPPH). Test agents were dissolved in 95% ethanol and were added to a solution of DPPH in 95% ethanol. The final concentration of both the test compound and DPPH was 0.4 mMol. Absorbance was continuously recorded on a Perkin-Elmer Lamba 4B spectrophotometer. The percent quench was measured thirty minutes following the combination of the two solutions. (*Free Rad. Res. Comms.*, volume 15, pages 91–100 (1991)).

| Compound | DPPH (% Quench) |
|---|---|
| Compound No. 1 | 99 |
| Compound No. 2 | 96 |
| BHT | 64 |
| Vitamin E | 87 |
| Flunarizine | 10* |

*value from Free Rad. Res. Comms., volume 15, pages 91–100, (1991), reported value for vitamin E 90%

Antioxidant activity was measured using a phospholipid oxidation assay. Liposomes formed from dilineoleolyl phosphocholine were exposed to Fe$^{+3}$/EDTA (167 µM) and ascorbate (167 µM). Oxidation was measured by conjugate diene formation monitored using UV spectroscopy (*Biochim. Biophys. Acta.*, volume 1081, pages 181–187, (1991)). The IC$_{50}$ was calculated using the following non-linear regression algorithm: $Y=A/[1+(B/X)^c]$, wherein A=maximum, B=IC$_{50}$ and c=cooperativity or relative broadness of the curves. The minimum was assumed to be zero.

| Compound | Phospholipid Oxidation IC$_{50}$ µM |
|---|---|
| Compound No. 1 | 3.6 |
| Compound No. 2 | 0.18 |
| BHT | 201. |
| Vitamin E | 4.2 |
| Flunarizine | 149 |

Antioxidant activity was also measured using a liver microsome assay (*Chem. Biol. Interactions.*, volume 74, pages 233–52, (1990)). Microsomes were incubated in a KPi buffer. Lipid oxidation was initiated with ADP(1 mM)/FeCl$_3$ (10 µM) and NADPH regenerating system, containing NADP$^+$. The lipid peroxidation was assayed by the TBA test. Malondialdehyde (MDA) was estimated by the formation of thiobarbituric acid-reactive substances. MDA-equivalents were calculated using $\epsilon$=156 mM$^-$cm$^{-1}$. IC$_{50s}$ were calculated using regression lines.

| Compound | Liver Microsomes IC$_{50}$ µM |
|---|---|
| Compound No. 1 | 1.0 |
| BHT | 1.1 |
| Vitamin E | 37 |
| Flunarizine | 27.1 |

Calcium binding was measured using a radioligand binding assay. Brain cortices were removed from rats and a membrane fraction was prepared by standard techniques. The membrane preparation was incubated with radiolabeled nitrendipine. Non-specific binding was estimated in the presence of non-labeled nitrendipine. Membranes were filtered and washed and the filters were counted to determine radiolabelled nitrendipinalcium channel in *Acad. Sci. USA*, volume 79, pages 3656–3660 (1982), *Life Sci.*, volume 30, pages 2191–2202, (1982).

| Compound | Ca$^{+2}$ Binding IC$_{50}$ µM |
|---|---|
| Compound No. 1 | 1–10 |
| Compound No. 2 | 1–10 |
| BHT | ND |
| Vitamin E | ND |
| Flunarizine | 1–10 |

ND = not determined

Calcium antagonist binding activity can be measured by measuring the effects of the compound on calcium flux through a voltage sensitive membrane (see *J. Cardiovascular Pharmacology*, volume 17, pages 41–53, (1991)), and references cited therein). Rat adrenal phenochromocytoma (PC12, American Type Culture Collection) or NG108 cells are cultured using standard techniques. Intracellular free calcium concentrations are determined using the fluorescent calcium indicator Fura-2 AM. The effects of the test drugs on depolarization induced stimulation of intracellular free calcium are determined in a balanced salt solution. Before stimulation, the cells are washed three times with buffer containing the test drug. After a 1 h incubation, potassium chloride is added to a final concentration of 50 mM. Data can be expressed as the percentage of intracellular free calcium obtained in the absence of drug with basal levels subtracted. The IC$_{50}$ value may be determined by analysis of the competition curves for at least six concentrations of drug.

The competition curve data can be analyzed using a nonlinear, least-squares best fit of the data to the Hill equation.

Calcium antagonist effect can also be measured by inhibiting calcium chloride induced contractions of endothelium-denuded spiral segments of rabbit thoracic aorta (see *J. Cardiovascular Pharmacology*, volume 17, pages 41–53, (1991), *Br. J. Pharmacal.* volume 6, pages 549–60, (1969)). Tissues are incubated in Krebs buffer containing the compound to be tested for 25 minutes. The pA$_2$ values can be determined by averaging the responses to three tissues and using the methods described in *Arch. Int. Pharmacodyn*, volume 3, pages 299–330, (1963).

The cytoprotective effects of the compounds were measured using bovine retinal pieces. Retinal tissues were incubated in hypoxic media for 1 h. After 50 minutes of hypoxia, test agents were added to the media to allow 10 minutes for the drug to diffuse into the tissue prior to reoxygenation. Vehicle was added to the non-drug group. Following the incubation period, the tissue was reoxygenated for 1 h. Lipid peroxidation was assessed by the formation of thiobarbituric acid reacting substances (TBARS). The tissues were homogenized and added to TCA-TBA reagent and heated in the presence of BHT. The homogenate was filtered and the absorbance of the supernatant was measured spectrophotometrically. A double derivative technique was used to calculate the concentration of TBARS present in each sample. Quantitation was based on molar extinction coefficient of $1.56 \times 10^5$.

| Compound | Retinal Pieces IC$_{50}$ µM |
|---|---|
| Compound No. 1 | 0.01 |
| Compound No. 2 | 0.05 |
| BHT | 0.5 |
| Vitamin E | 0.001 |
| Flunarizine | ND |

ND = not determined

The retinoprotective properties of the compounds were measured in a light damage model. Photochemical lesions were induced in free moving unanesthetized albino rats by a single 48 h continuous broad-band florescent visible-light exposure. The rats were dosed by intraperitoneal injection 48 and 24 h prior to exposure, every 24 h during the exposure and once during the 24 h recovery period. Ocular tissues were obtained 24 h after light exposure. The tissues were analyzed using a quantitative computer image analyses system attached to the microscope. Retinal layer thickness, number of macrophages in the subretinal space, number of pyknotic nuclei in the outer nuclear layer, and retinal layer areas were parameters that were measured and statistically analyzed.

Ocular function was measured using electroretinography. Rats were anesthetized after a four-day recovery period in the dark. Flash ERGs were elicited by viewing a ganzfield. Electrical responses to a series of light flashes increasing in intensity were digitized to analyze response voltage-log intensity relationships.

Control rats remaining on their normal 12 h light/12 h dark light cycle were devoid of retinal lesions upon microscopic examination and were assessed to have normal retinal function. However, 48 h continuous fluorescent broad-band visible-light exposure resulted in irreversible loss of photoreceptor cells, RPE necrosis, and blood-retinal barrier breakdown. Damage to photoreceptor cells was significantly minimized and RPE damage was greatly reduced in rats treated with Compound No. 1. Macrophages in the subretinal space were not greater than control values and significantly reduced when compared to non-dosed light exposed rats. Analysis of photoreceptor length indicated that Compound No. 1 prevented outer and inner segment damage. The number of pyknotic photoreceptor nuclei was reduced by 50% in the outer nuclear layer compared to non-dosed animals.

Retinal function was assessed by measuring the electroretinogram after 48 h light exposure. The ERG allows differential examination of photoreceptor activity (a-wave) and inner nuclear layer function (b-wave) which is correlated to retinal morphology change. After light exposure, the ERG a-wave and b-wave amplitudes are significantly diminished by approximately 80%. Significant preservation of retinal function was measured in rats dosed with Compound No. 1.

The singlet oxygen quenching activity was studied in the following manner. Singlet oxygen was generated chemically by using thermodissociation of the endoperoxide 3,3'-(1,4-naphthylidene dipropionate), $NPDO_2$. At 37° C., 3 ml ethanol/chloroform (50:50) were placed in a thermosrated cuvette. Reactions were started by injection of 5 mM $NDPO_2$. The singlet oxygen quenching constants were calculated according to Stern-Volmer plots, from $S_0/S=1+(Kq+KR)*[Q]*I$, where $S_0$, S—chemiluminesence (1270 nm) intensities in absence and in the presence of quenchers, respectively, [Q} is the quencher concentration and I is the lifetime of singlet oxygen (see *J. Amer. Chem.*, volume 111, pages 2904–2914, (1989)).

| Compound | Singlet Oxygen Quenching $Kq \times 10^8$ ($M^{-1}$ $*s^{-1}$) |
|---|---|
| Compound No. 1 | ND |
| Compound No. 2 | 1.6 |
| BHT | IA |
| Vitamin E | 1.2 |
| Flunarizine | 0.05 |

ND = not determined
IA = inactive

EXAMPLE 7

Formulations

The following formulation is provided to further illustrate the pharmaceutical compositions of the present invention, particularly compositions intended for topical application to the eye. In this example, the term "Compound" is intended to represent any of the compounds of formula (I) above.

| Ingredient | Amount (wt. %) | Purpose |
|---|---|---|
| Compound (free base) | 1.0 | Active ingredient |
| Polyvinyl alcohol, USP | 1.4 | Excipient |
| Monobasic sodium phosphate (Monohydrate), USP | 0.05 | Buffering agent |
| Dibasic Sodium Phosphate (Anhydrous), USP | 0.15 | Buffering agent |
| Sodium chloride, USP | 0.5 | Tonicity agent |
| Disodium EDTA (Edetate disodium), USP | 0.01 | Preservative |
| Polysorbate 80, NF | 0.05 | Surfactant |
| Benzalkonium chloride solution, NF | 0.01 + 5 excess | Preservative |
| Sodium hydroxide, NF | q.s. | pH adjustment |
| Hydrochloric acid, NF | q.s. | pH adjustment |
| Water for injection, USP | q.s. 100 | Vehicle |

What is claimed is:
1. A compound of the formula:

A—Y—B wherein:
A is an antioxidant selected from the group consisting of:

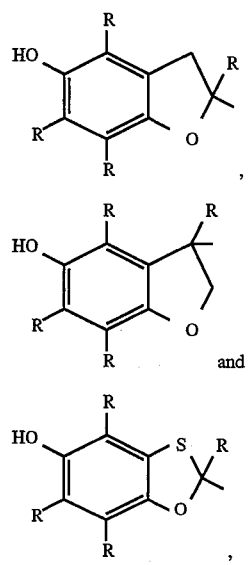

wherein R is $C_1$ to $C_6$ alkyl;
Y is $(CH_2)_n$ or $CH=CH(CH_2)_n$, wherein n is a whole number of from 1 to 6; and
B is selected from the group consisting of:

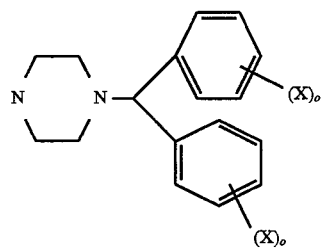

and

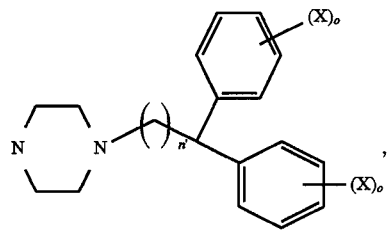

wherein:
n' is a whole number of from 1 to 6;
X is F, Cl, I, Br, OH, OR', SH, $S(O)_mR'$, CN or $NO_2$, wherein R' is $C_1$ to $C_6$ alkyl and m is 0, 1 or 2; and o is 0, 1, 2 or 3, or a pharmaceutically acceptable salt thereof.

2. A compound according to claim 1, wherein A is

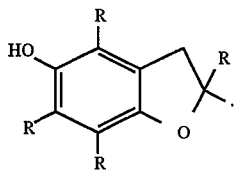

3. A compound according to claim 2, wherein R is methyl.

4. A compound according to claim 1, wherein X is F, Cl, CN, $S(O)_mR'$ or OR', wherein m is 1 or 2 and R' is $C_1$ to $C_4$ alkyl.

5. A compound according to claim 4, wherein A is:

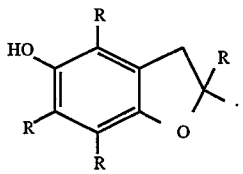

6. A compound according to claim 5, wherein R is methyl.

7. A compound according to claim 1, wherein B is:

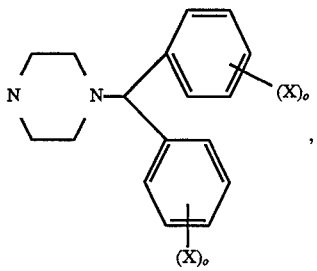

and A is:

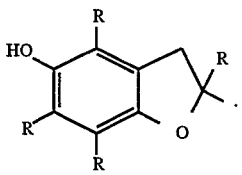

8. A compound according to claim 7, wherein X is F, Cl, CN, $S(O)_mR'$ or OR', wherein m is 1 or 2 and R' is $C_1$ to $C_4$ alkyl.

9. A compound according to claim 8, wherein R is methyl.

10. A compound according to claim 9, wherein X is fluoro.

11. A compound according to claim 10, wherein Y is $(CH_2)_n$.

12. A compound according to claim 11, wherein n is 2.

13. A compound according to claim 12, wherein the compound has the following formula:

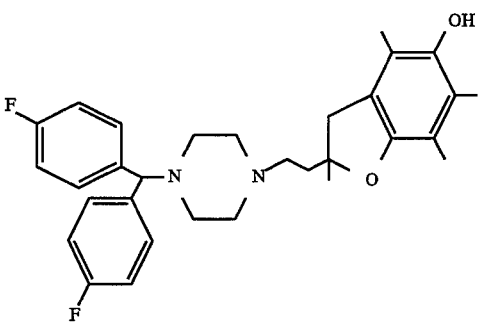

14. A pharmaceutical composition for preventing or alleviating damage to mammalian tissues, comprising an amount of a compound of the following formula effective to decrease free radical or oxidative damage and control intracellular free calcium levels in said tissues:

A—Y—B wherein:

A is an antioxidant selected from the group consisting of:

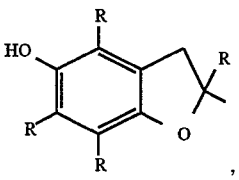

,

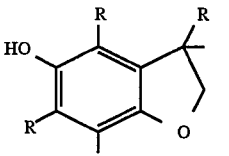

and

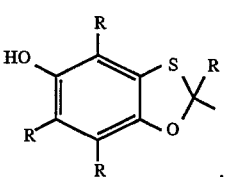

, wherein R is $C_1$ to $C_6$ alkyl;

Y is $(CH_2)_n$ or $CH=CH(CH_2)_n$, wherein n is a whole number of from 1 to 6; and B is selected from the group consisting of:

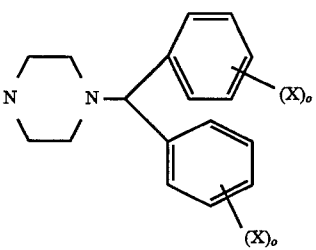

and

-continued

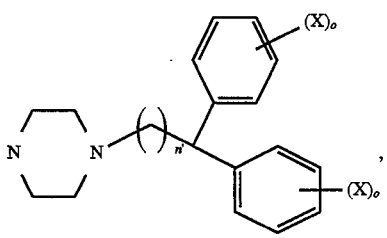

wherein:

n' is a whole number of from 1 to 6;

X is F, Cl, I, Br, OH, OR', SH, S(O)$_m$R', CN or NO$_2$, wherein R' is C$_1$ to C$_6$ alkyl and m is 0, 1 or 2; and o is 0, 1, 2 or 3, or a pharmaceutically acceptable salt thereof; and a pharmaceutically acceptable vehicle therefor.

15. A composition according to claim 14, wherein A is

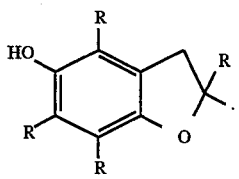

16. A composition according to claim 15, wherein R is methyl.

17. A composition according to claim 14, wherein X is F, Cl, CN, S(O)$_m$R' or OR', wherein m is 1 or 2 and R' is C$_1$ to C$_4$ alkyl.

18. A composition according to claim 17, wherein A is:

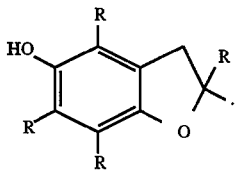

19. A composition according to claim 18, wherein R is methyl.

20. A composition according to claim 14, wherein B is:

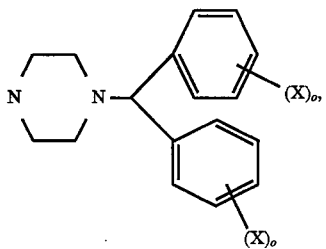

and A is:

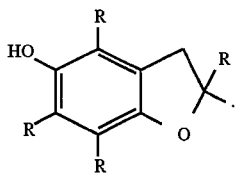

21. A composition according to claim 20, wherein X is F, Cl, CN, S(O)$_m$R' or OR', wherein m is 1 or 2 and R' is C$_1$ to C$_4$ alkyl.

22. A composition according to claim 21, wherein R is methyl.

23. A composition according to claim 22, wherein X is fluoro.

24. A composition according to claim 23, wherein Y is (CH$_2$)$_n$.

25. A composition according to claim 24, wherein n is 2.

26. A composition according to claim 25, wherein the compound has the following formula:

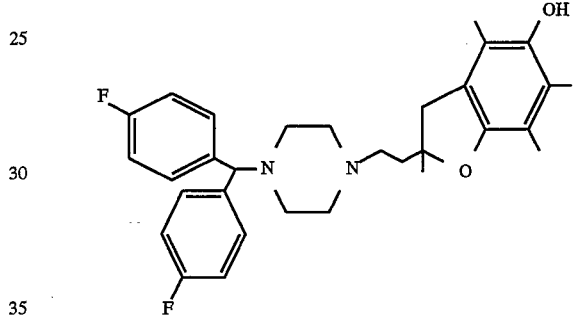

27. A composition according to claim 14, wherein the pharmaceutically acceptable vehicle comprises a physiologically balanced irrigating solution.

28. A method of preventing or reducing damage to ophthalmic tissues at the cellular level, which comprises administering to the eye of a human patient a therapeutically effective amount of a composition comprising 0.001 to 5 wt. % of a compound of the following formula:

A—Y—B wherein:

A is an antioxidant selected from the group consisting of:

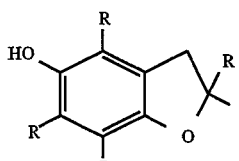

,

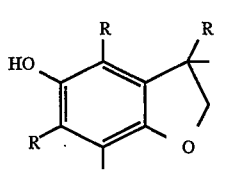

and

-continued

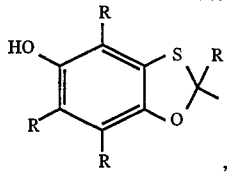

wherein R is $C_1$ to $C_6$ alkyl;

Y is $(CH_2)_n$ or $CH=CH(CH_2)_n$, wherein n is a whole number of from 1 to 6; and B is selected from the group consisting of:

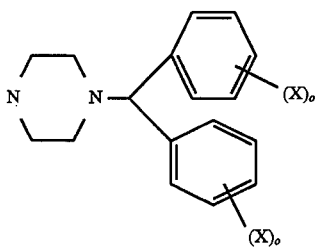

and

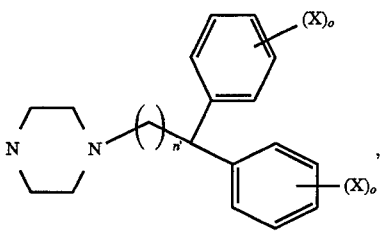

wherein:

n' is a whole number of from 1 to 6;

X is F, Cl, I, Br, OH, OR', SH, $S(O)_mR'$, CN or $NO_2$, wherein R' is $C_1$ to $C_6$ alkyl and m is 0, 1 or 2; and o is 0, 1, 2 or 3, or a pharmaceutically acceptable salt thereof; and a pharmaceutically acceptable vehicle therefor.

29. A method according to claim 28, wherein B is:

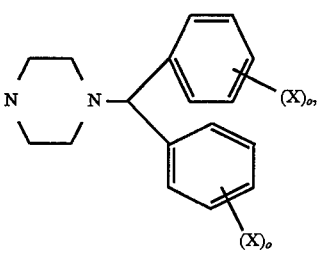

and A is:

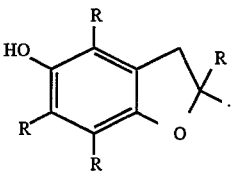

30. A method according to claim 29, wherein X is F, Cl, CN, $S(O)_mR'$ or OR', wherein m is 1 or 2 and R' is $C_1$ to $C_4$ alkyl.

31. A method according to claim 30, wherein R is methyl.

32. A method according to claim 31, wherein X is fluoro.

33. A method according to claim 32, wherein Y is $(CH_2)_n$.

34. A method according to claim 33, wherein n is 2.

35. A method according to claim 34, wherein the compound has the following formula:

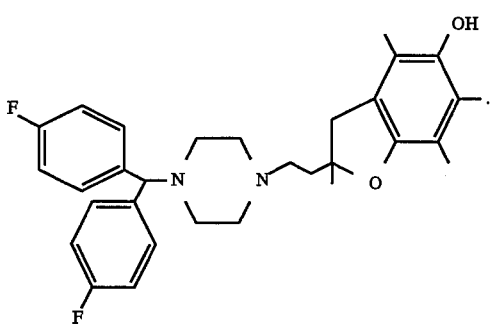

36. A method according to claim 28, wherein the composition is administered in an amount of 0.01 to 100 mg/kg, one to four times per day.

37. A method according to claim 28, wherein the composition is administered by means of topical application to the affected ophthalmic tissues.

38. A method according to claim 37, wherein the composition is administered to the patient in conjunction with an ophthalmic surgical procedure.

39. A method according to claim 38, wherein the pharmaceutically acceptable vehicle comprises a physiologically balanced irrigating solution.

40. A method according to claim 39, wherein the composition is administered to the patient during an intraocular surgical procedure.

* * * * *